(12) United States Patent
Dairaghi et al.

(10) Patent No.: US 10,786,494 B2
(45) Date of Patent: *Sep. 29, 2020

(54) CCR6 COMPOUNDS

(71) Applicant: CHEMOCENTRYX, INC., Mountain View, CA (US)

(72) Inventors: Daniel Dairaghi, Palo Alto, CA (US); Dean R. Dragoli, Los Altos, CA (US); Jaroslaw Kalisiak, Mountain View, CA (US); Christopher W. Lange, El Cerrito, CA (US); Manmohan Reddy Leleti, Dublin, CA (US); Yandong Li, San Diego, CA (US); Rebecca M. Lui, Santa Clara, CA (US); Venkat Reddy Mali, Cupertino, CA (US); Viengkham Malathong, Mountain View, CA (US); Jay P. Powers, Pacifica, CA (US); Hiroko Tanaka, Mountain View, CA (US); Joanne Tan, San Franciso, CA (US); Matthew J. Walters, Pacifica, CA (US); Ju Yang, Palo Alto, CA (US); Penglie Zhang, Foster City, CA (US)

(73) Assignee: ChemoCentryx, Inc., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/150,796

(22) Filed: Oct. 3, 2018

(65) Prior Publication Data

US 2019/0167659 A1    Jun. 6, 2019

Related U.S. Application Data

(63) Continuation of application No. 15/709,012, filed on Sep. 19, 2017, now Pat. No. 10,117,865, which is a continuation of application No. 15/074,965, filed on Mar. 18, 2016, now Pat. No. 9,795,599, which is a continuation of application No. 14/557,949, filed on Dec. 2, 2014, now Pat. No. 9,340,509.

(60) Provisional application No. 61/910,838, filed on Dec. 2, 2013.

(51) Int. Cl.
| | |
|---|---|
| *A61K 31/47* | (2006.01) |
| *C07D 215/48* | (2006.01) |
| *C07D 405/04* | (2006.01) |
| *C07D 405/14* | (2006.01) |
| *A61K 31/4709* | (2006.01) |

(52) U.S. Cl.
CPC .......... *A61K 31/47* (2013.01); *A61K 31/4709* (2013.01); *C07D 215/48* (2013.01); *C07D 405/04* (2013.01); *C07D 405/14* (2013.01)

(58) Field of Classification Search
CPC ..... C07D 215/48; C07D 405/04; A61K 31/47
USPC ....................................................... 514/311
See application file for complete search history.

(56) References Cited

U.S. PATENT DOCUMENTS

| | | | |
|---|---|---|---|
| 3,944,553 | A | 3/1976 | O'Rell |
| 4,021,409 | A | 5/1977 | Arnold |
| 8,546,405 | B2 | 10/2013 | DeGoey et al. |
| 9,340,509 | B2 | 5/2016 | Dairaghi et al. |
| 9,795,599 | B2 | 10/2017 | Dairaghi et al. |
| 10,117,865 | B2 | 11/2018 | Dairaghi et al. |
| 2009/0233946 | A1 | 9/2009 | Krasinski et al. |
| 2010/0256145 | A1 | 10/2010 | Bak-Jensen et al. |

FOREIGN PATENT DOCUMENTS

| | | | |
|---|---|---|---|
| CN | 101820881 A | 9/2010 | |
| JP | 2007-537275 A | 12/2007 | |
| JP | 2008-526996 A | 7/2008 | |
| JP | 2010-504280 A | 2/2010 | |
| JP | 2010-504908 A | 2/2010 | |
| JP | 2010-533203 A | 10/2010 | |
| JP | 2011-513196 A | 4/2011 | |
| JP | 2011-522806 A | 8/2011 | |
| WO | 2005/113513 A2 | 12/2005 | |
| WO | 2005/113513 A3 | 12/2005 | |
| WO | WO-2005113513 A2 * | 12/2005 | ........... C07C 311/21 |
| WO | 2006/076644 A2 | 7/2006 | |
| WO | 2006/076644 A3 | 7/2006 | |
| WO | WO-2006076644 A2 * | 7/2006 | ........... C07C 311/21 |

(Continued)

OTHER PUBLICATIONS

Statins inhiobit chemotactic interaction between CCL20 and CCR6 in vitro: possible relevance to psoriasis treatment. (Year: 2011).*

(Continued)

*Primary Examiner* — Rita J Desai

(74) *Attorney, Agent, or Firm* — Mintz Levin Cohn Ferris Glovsky and Popeo PC

(57) ABSTRACT

Compounds of formula (I) are provided which are useful in the treatment of diseases or conditions modulated at least in part by CCR6:

5 Claims, 11 Drawing Sheets

Specification includes a Sequence Listing.

(56) References Cited

FOREIGN PATENT DOCUMENTS

| WO | 2008/008375 A2 | 1/2008 |
|---|---|---|
| WO | 2008/008375 A3 | 1/2008 |
| WO | 2008/010934 A2 | 1/2008 |
| WO | 2008/010934 A3 | 1/2008 |
| WO | 2009/008552 A1 | 1/2009 |
| WO | 2009/009740 A1 | 1/2009 |
| WO | 2009/015667 A1 | 2/2009 |
| WO | 2009/141386 A1 | 11/2009 |
| WO | 2009/155121 A2 | 12/2009 |
| WO | 2009/155121 A3 | 12/2009 |
| WO | 2011/031896 A2 | 3/2011 |
| WO | 2011/031896 A3 | 3/2011 |
| WO | 2011/067272 A1 | 6/2011 |
| WO | 2011/119518 A1 | 9/2011 |
| WO | 2012/050985 A1 | 4/2012 |
| WO | 2012/102544 A2 | 8/2012 |
| WO | 2012/102544 A3 | 8/2012 |
| WO | 2012/176856 A2 | 12/2012 |
| WO | 2012/176856 A3 | 12/2012 |
| WO | 2013/026933 A1 | 2/2013 |
| WO | 2013/061004 A1 | 5/2013 |
| WO | 2013/061005 A1 | 5/2013 |
| WO | 2013/130811 A | 9/2013 |

OTHER PUBLICATIONS

Extended European Search Report corresponding to EP Application No. 14867718.0 dated Mar. 14, 2017, 9 pages.

International Search Report and Written Opinion corresponding to International Application No. PCT/US2014/068152, dated Feb. 18, 2015, 8 pages.

Ayers, Chris M. et al., "Increased presence of dendritic cell chemokines in the sinus mucosa of chronic rhinosinusitis with nasal polyps and allergic fungal rhinosinusitis,." *International Forum of Allergy & Rhinology* (Jul./Aug. 2011); 1(4):296-302 [accepted Dec. 14, 2010.].

Blazquez, Ana Belén et al., "A Functional Role for CCR6 on Proallergic T Cells in the Gastrointestinal Tract," *Gastroenterology* (2010); 138(1):275-284 [doi:10.1053/j.gastro.2009.09-016].

Carbone, Teresa et al., "$CD56^{high}CD16^-CD62L^-$ NK Cells Accumulate in Allergic Contact Dermatitis and Contribute to the Express of Allergic Responses," *The Journal of Immunology* (2010); 184:1102-1110 [prepublished online Dec. 11, 2009].

Czaja, A. J., "Review article: chemokines as orchestrators of autoimmune hepatitis and potential therapeutic targets," *Ailment Pharmacol Ther* (2014); 40:261-279 [EV Pub Online Jun. 2, 2014].

Demedts, Ingel K. et al., "Accumulation of Dendritic Cells and Increased CCL20 Levels in the Airways of Patients with Chronic Obstructive Pulmonary Disease," *American Journal of Respiratory and Critical Care Medicine* (2007); 175:998-1005 [originally published Mar. 1, 2007].

Deng, Jiusheng et al., "TLR4 and TLR5 induce distinct types of vasculitis," *Cir Res.* (Feb. 27, 2009); 104(4):488-495.

Facco, Monica et al., "Sarcoidosis is a Th1/Th17 multisystem disorder," *Thorax* (2011); 66:144-150 [published online first Dec. 7, 2010].

Fichorova, Raina N. et al., "*Trichomonas vaginalis* Lipophosphoglycan Triggers a Selective Upregulation of Cytokines by Human Female Reproductive Tract Epithelial Cells," *Infection and Immunity* (Oct. 2006); 74(10):5773-5779 [accepted Jul. 23, 2006].

Gao, Jianming et al., "mRNA profiles of cytokine receptors in unstimulated peripheral blood mononuclear cells from patients with chronic idiopathic urticarial," *Journal of Biomedical Research* (2011); 25(2):141-147 [accepted Feb. 26, 2011].

Gros, Eva et al., "Expression of chemokines and chemokine receptors in lesional and nonlesional upper skin of patients with atopic dermatitis," *J Allergy Clin Immunol* (Oct. 2009); 124:753-760 [accepted for publication Jul. 6, 2009].

Honkanen, Jarno et al., "IL-17 Immunity in Human Type 1 Diabetes," *J Immunol* (2010) 185:1959-1967 [prepublished online Jun. 30, 2010].

Jin, Ying et al., "Common variants in FOXP1 are associated with generalized vitiligo," *Nature Genetics* (Jul. 2010) 42(7):576-578 [published online Jun. 6, 2010].

Kerzel, Sebastian et al., "$T_H17$ Cell Frequency in Peripheral Blood from Children with Allegic Asthma Correlates with the Level of Asthma Control," *J Pediatr* (2012) 161:1172-1174 [accepted Jul. 25, 2012].

Klein, Matthias et al., "Leukocyte Attraction by CCL20 and Its Receptor CCR6 in Humans and Mice with Pneumococcal Meningitis," *PLOS One* (Apr. 3, 2014) 9(4):e93057 (10 pages).

Koumakis, Eugénie et a., "A Regulatory Variant in CCR6 is Associated With Susceptibility to Antitopoisomerase-Positive Systemic Sclerosis," *Arthritits & Rheumatism* (Dec. 2013); 65(12):3202-3208 [accepted in revised form Aug. 13, 2013].

Lee, Adrian Y. S. et al., "CC chemokine ligand 20 and its cognate receptor CCR6 in mucosal T cell immunology and inflammatory bowel disease: odd couple or axis of evil?" *Frontiers in Immunology* (Jul. 15, 2013); 4:194 (10 pages).

Li, Xiaoli et al., "Chemokine (C-C Motif) Ligand 20, a Potential Biomarker for Graves' Disease, is Regulated by Osteopontin," *PLOS One* (May 22, 2013); 8(5):e64277 (8 pages).

Mabuchi, Tomotaka et al., "Epidermal CCR6$^+$ γδ T Cells Are Major Producers of IL-22 and IL-17 in a Murine Model of Psoriasiform Dermatitis," *J Immunol* (2011); 187:5026-5031 [prepublished online Oct. 7, 2011].

Nakayama, Takashi et al., "Inducible expression of a CC chemokine liver- and activation-regulated chemokine (LARC)/macrophage inflammatory protein (MIP)-3α/CCL20 by epidermal keratinocytes and its role in atopic dermatitis," *International Immunology* (accepted Oct. 5, 2000); 13(1):95-103.

Nalbant, Ayten et al., "Genes associated with T helper 17 cell differentiation and function," *Frontiers in Bioscience, Elite* (Jun. 1, 2016) 8:427-435.

Oo, Ye Htun et al., "CXCR3-dependent recruitment and CCR6-mediated positioning of Th-17 cells in the inflamed liver," *Journal of Hepatology* (2012) 57:1044-1051 [accepted Jul. 5, 2012].

Paradis, Timothy J. et al., "Essential Role of CCR6 in Directing Activated T Cells to the Skin during Contact Hypersensitivity," *Journal of Investigative Dermatology* (2008) 218:628-633 [published online Sep. 20, 2007].

Puleston, J. et al., "A distinct subset of chemokines dominates the mucosal chemokine response in inflammatory bowel disease," *Aliment Pharmacol Ther* (2005); 21:109-120 [accepted for publication Sep. 14, 2004].

Skovdahl, Helen Kolstad et al., "Expression of CCL20 and Its Corresponding Receptor CCR6 is Enhanced in Active Inflammatory Bowel Disease, and TLR3 Mediates CCL20 Expression in Colonic Epithelial Cells," *PLOS One* (Nov. 4, 2015); 10(11):e0141710 (17 pages).

Subramanian, Sandhya et al., "CCR6: A biomarker for Alzheimer's-like disease in a triple transgenic mouse model," *J Alzheimers Dis.* (Jan. 1, 2010); 22(2):619-629.

Tsai, Wen-Hui et al., "Plasma levels in sepsis patients of annexin A1, lipoxin A4, macrophage inflammatory protein-3a, and neutrophil gelatinase-associated lipocalin," *Journal of the Chinese Medical Associate* (Jan. 31, 2013); 76:486-490.

Turner, Jan-Eric et al., "CCR6 Recruits Regulatory T Cells and Th17 Cells to the Kidney in Glomerulonephritis," *J Am Soc Nephrol* (2010) 21:974-985 [accepted Jan. 27, 2010].

Van Der Waart et al., "Decreased Levels of Circulating IL17-Producing CD161$^+$CCR6$^+$ T Cells are Associated with Graft-versus-Host Disease after Allogeneic Stem Cell Transplantation," *PLOS One* (Dec. 4, 2012); 7(12):e50896 (13 pages).

Wan, Wuzhou et al., "Genetic Deletion of Chemokine Receptor Ccr6 Decreases Atherogenesis in ApoE-deficient Mice," *Cir Res.* (Aug. 5, 2011); 109(4):374-381.

Welsh-Bacic, Desa et al., "Expression of the chemokine receptor CCR6 in human renal inflammation," *Nephrol Dial Translation* (2011) 26:1211-1220 [Advance Access publication Sep. 15, 2010].

(56) References Cited

OTHER PUBLICATIONS

Woltman, Andrea M. et al., "MIP-3α/CCL20 in Renal Transplantation and Its Possible Involvement as Dendritic Cell Chemoattractant in Allograft Rejection," *American Journal of Transplantation* (2005) 5:2114-2125 [accepted for publication Apr. 25, 2005].

Wright, Pamela B. et al., "Ankylosing spondylitis patients display altered dendritic cell and T cell populations that implicate pathogenic roles for the IL-23 cytokine axis and intestinal inflammation," *Rheumatology* (2016) 55:120-132 [Advance Access publication Aug. 28, 2015].

Zhang, Ruan et al., "Requirement for CD28 in Effector Regulatory T Cell Differentiation, CCR6 Induction, and Skin Homing," *J Immunol* (2015) 195:4154-4161 [prepublished online Sep. 25, 2015].

Zhou, Xu-jie et al., "Association of variants in CCR6 with susceptibility to lupus nephritis in Chinese," *Arthritis & Rheumatology* (Nov. 2015) 67(11):3091-3093 [first published Oct. 28, 2015].

\* cited by examiner

FIG. 1A

TABLE 1: Compound Potency in the L1.2 CCR6 Binding Assay

| Number | Structure | Potency | Number | Structure | Potency |
|---|---|---|---|---|---|
| 1.001 | | ++ | 1.010 | | ++ |
| 1.002 | | + | 1.011 | | + |
| 1.003 | | ++ | 1.012 | | + |
| 1.004 | | + | 1.013 | | ++ |
| 1.005 | | + | 1.014 | | + |
| 1.006 | | + | 1.015 | | + |
| 1.007 | | + | 1.016 | | + |
| 1.008 | | + | 1.017 | | + |
| 1.009 | | + | 1.018 | | + |

FIG. 1B

TABLE 1: Compound Potency in the L1.2 CCR6 Binding Assay

| Number | Structure | Potency | Number | Structure | Potency |
|---|---|---|---|---|---|
| 1.019 | 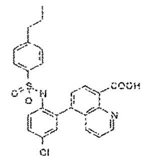 | + | 1.026 | 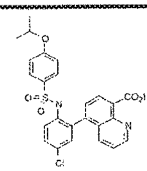 | + |
| 1.020 | 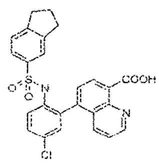 | + | 1.027 | 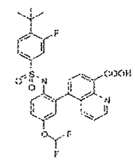 | + |
| 1.021 | 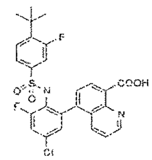 | + | 1.028 | 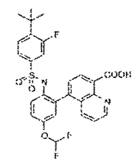 | +++ |
| 1.022 | 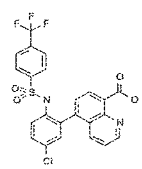 | + | 1.029 | 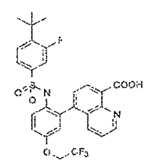 | + |
| 1.023 | 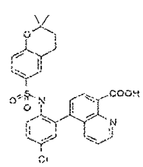 | + | 1.030 | 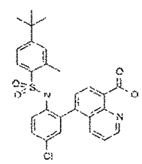 | + |
| 1.024 | 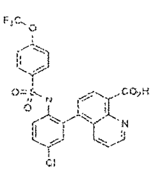 | + | 1.031 | 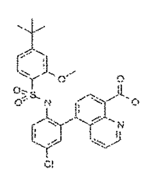 | + |
| 1.025 | 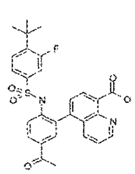 | + | 1.032 | 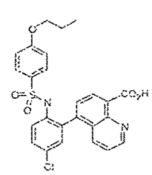 | + |

FIG. 1C

TABLE 1: Compound Potency in the L1.2 CCR6 Binding Assay

| Number | Structure | Potency | Number | Structure | Potency |
|---|---|---|---|---|---|
| 1.033 | | ++ | 1.040 | | + |
| 1.034 | | ++ | 1.041 | | + |
| 1.035 | | + | 1.042 | | + |
| 1.036 | | + | 1.043 | | + |
| 1.037 | | + | 1.044 | | + |
| 1.038 | | + | 1.045 | | + |
| 1.039 | | + | 1.046 | | + |

FIG. 1D

TABLE 1: Compound Potency in the L1.2 CCR6 Binding Assay

| Number | Structure | Potency | Number | Structure | Potency |
|---|---|---|---|---|---|
| 1.047 | | + | 1.054 | | + |
| 1.048 | | + | 1.055 | | ++ |
| 1.049 | | ++ | 1.056 | | + |
| 1.050 | | + | 1.057 | | ++ |
| 1.051 | | + | 1.058 | | + |
| 1.052 | | ++ | 1.059 | | + |
| 1.053 | | ++ | 1.060 | | + |

FIG. 1E

TABLE 1: Compound Potency in the L1.2 CCR6 Binding Assay

| Number | Structure | Potency | Number | Structure | Potency |
|---|---|---|---|---|---|
| 1.061 | | ++ | 1.068 | | + |
| 1.062 | | ++ | 1.069 | | ++ |
| 1.063 | | + | 1.070 | | + |
| 1.064 | | + | 1.071 | | + |
| 1.065 | | + | 1.072 | | +++ |
| 1.066 | | + | 1.073 | | + |
| 1.067 | | + | 1.074 | | ++ |

FIG. 1F

TABLE 1: Compound Potency in the L1.2 CCR6 Binding Assay

| Number | Structure | Potency | Number | Structure | Potency |
|---|---|---|---|---|---|
| 1.075 | | +++ | 1.082 | | ++ |
| 1.076 | | ++ | 1.083 | | +++ |
| 1.077 | | + | 1.084 | | ++ |
| 1.078 | | + | 1.085 | | ++ |
| 1.079 | | + | 1.086 | | ++ |
| 1.080 | | +++ | 1.087 | | ++ |
| 1.081 | | ++ | 1.088 | | + |

FIG. 1G

TABLE 1: Compound Potency in the L1.2 CCR6 Binding Assay

| Number | Structure | Potency | Number | Structure | Potency |
|---|---|---|---|---|---|
| 1.089 | 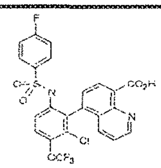 | + | 1.096 | 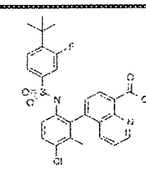 | + |
| 1.090 | 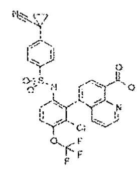 | + | 1.097 | 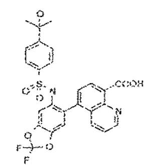 | + |
| 1.091 | 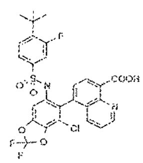 | +++ | 1.098 | 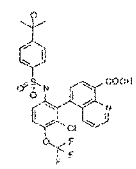 | ++ |
| 1.092 | 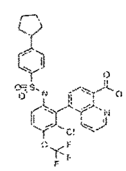 | +++ | 1.099 | 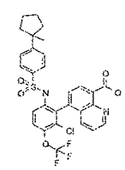 | +++ |
| 1.093 | 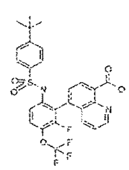 | ++ | 1.100 | 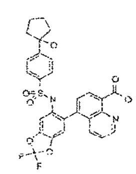 | + |
| 1.094 | 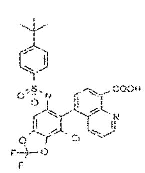 | +++ | 1.101 | 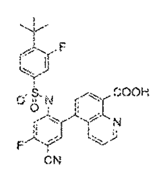 | + |
| 1.095 | 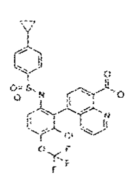 | ++ | 1.102 | 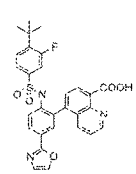 | + |

FIG. 1H

TABLE 1: Compound Potency in the L1.2 CCR6 Binding Assay

| Number | Structure | Potency | Number | Structure | Potency |
|---|---|---|---|---|---|
| 1.103 | 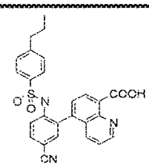 | + | 1.105 | 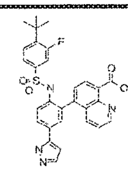 | + |
| 1.104 | 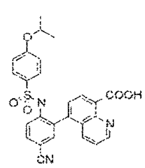 | + | 1.106 | 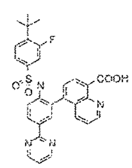 | + |

FIG. 2A

TABLE 2: Compound Potency in the KHGY-1 Cell Migration Assay

| Number | Structure | Potency | Number | Structure | Potency |
|---|---|---|---|---|---|
| 1.107 | | +++ | 1.115 | | + |
| 1.108 | | + | 1.116 | | +++ |
| 1.109 | | +++ | 1.117 | | +++ |
| 1.110 | | +++ | 1.118 | | +++ |
| 1.111 | | +++ | 1.119 | | +++ |
| 1.112 | | +++ | 1.120 | | ++ |
| 1.113 | | + | 1.121 | | + |
| 1.114 | | ++ | 1.122 | | +++ |

FIG. 2B

TABLE 2: Compound Potency in the KHGY-1 Cell Migration Assay

| Number | Structure | Potency | Number | Structure | Potency |
|---|---|---|---|---|---|
| 1.123 | | +++ | 1.131 | | + |
| 1.124 | | +++ | 1.132 | | + |
| 1.125 | | + | 1.133 | | + |
| 1.126 | | ++ | 1.134 | | + |
| 1.127 | | + | 1.135 | | +++ |
| 1.128 | | ++ | 1.136 | | +++ |
| 1.129 | | + | 1.137 | | + |
| 1.130 | | + | 1.138 | | + |

FIG. 2C

TABLE 2: Compound Potency in the KHGY-1 Cell Migration Assay

| Number | Structure | Potency | Number | Structure | Potency |
|---|---|---|---|---|---|
| 1.139 | | +++ | 1.143 | | + |
| 1.140 | | + | 1.144 | | ++ |
| 1.141 | | ++ | 1.145 | | + |
| 1.142 | | +++ | | | |

SEQUENCE LISTING

<160> NUMBER OF SEQ ID NOS: 3

<210> SEQ ID NO 1
<211> LENGTH: 3216
<212> TYPE: DNA
<213> ORGANISM: Homo sapiens
<220> FEATURE:
<223> OTHER INFORMATION: chemokine (C-C motif) receptor 6 (CCR6, C-C
      CKR-6), transcript variant 1, chemokine receptor-like 3 (CKR-L3),
      G-protein-coupled receptor 29 (GPR29), seven-transmembrane receptor, lymphocyte, 22 (STRL22), LARC receptor, CD196, CMKBR6, DCR2, DRY6, GPRCY4

<400> SEQUENCE: 1

| | | | | | |
|---|---|---|---|---|---|
| agtgtatggg | tgaaggaggc | agcagtgtgg | ccggagagga | gagctgggct | gggagcacag | 60 |
| gaaggtcccc | aggactctgt | ggtcatcagt | aagagagggc | ccacgtgtat | atgctggtga | 120 |
| acagaaatgt | caacctttc | aaagtctgac | atttaagaga | aaaaactgtg | gctgttggtt | 180 |
| tgtggaacag | acagctcctt | ctttattgag | tcacctctac | tttcctgcta | ccgctgcctg | 240 |
| tgagctgaag | gggctgaacc | atacactcct | ttttctacaa | ccagcttgca | ttttttctgc | 300 |
| ccacaatgag | cggggaatca | atgaatttca | gcgatgtttt | cgactccagt | gaagattatt | 360 |
| ttgtgtcagt | caatacttca | tattactcag | ttgattctga | gatgttactg | tgctccttgc | 420 |
| aggaggtcag | gcagttctcc | aggctatttg | taccgattgc | ctactccttg | atctgtgtct | 480 |
| ttggcctcct | ggggaatatt | ctggtggtga | tcacctttgc | tttttataag | aaggccaggt | 540 |
| ctatgacaga | cgtctatctc | ttgaacatgg | ccattgcaga | catcctcttt | gttcttactc | 600 |
| tcccattctg | ggcagtgagt | catgccaccg | tgcgtgggt | tttcagcaat | gccacgtgca | 660 |
| agttgctaaa | aggcatctat | gccatcaact | ttaactgcgg | gatgctgctc | ctgacttgca | 720 |
| ttagcatgga | ccggtacatc | gccattgtac | aggcgactaa | gtcattccgg | ctccgatcca | 780 |
| gaacactacc | gcgcagcaaa | atcatctgcc | ttgttgtgtg | ggggctgtca | gtcatcatct | 840 |
| ccagctcaac | ttttgtcttc | aaccaaaaat | acaacaccca | aggcagcgat | gtctgtgaac | 900 |
| ccaagtacca | gactgtctcg | gagcccatca | ggtggaagct | gctgatgttg | gggcttgagc | 960 |
| tactctttgg | tttctttatc | cctttgatgt | tcatgatatt | ttgttacacg | ttcattgtca | 1020 |
| aaaccttggt | gcaagctcag | aattctaaaa | ggcacaaagc | catccgtgta | atcatagctg | 1080 |
| tggtgcttgt | gtttctggct | tgtcagattc | ctcataacat | ggtcctgctt | gtgacggctg | 1140 |
| caaatttggg | taaaatgaac | cgatcctgcc | agagcgaaaa | gctaattggc | tatacgaaaa | 1200 |
| ctgtcacaga | agtcctggct | ttcctgcact | gctgcctgaa | ccctgtgctc | tacgcttta | 1260 |
| ttgggcagaa | gttcagaaac | tactttctga | agatcttgaa | ggaccgtgtg | tgtgtgagaa | 1320 |
| ggaagtacaa | gtcctcaggc | ttctcctgtg | ccgggaggta | ctcagaaaac | atttctcggc | 1380 |
| agaccagtga | gaccgcagat | aacgacaatg | cgtcgtcctt | cactatgtga | tagaaagctg | 1440 |
| agtctcccta | aggcatgtgt | gaaacatact | catagatgtt | atgcaaaaaa | aagtctatgg | 1500 |
| ccaggtatgc | atggaaaatg | tgggaattaa | gcaaaatcaa | gcaagcctct | ctcctgcggg | 1560 |
| acttaacgtg | ctcatgggct | gtgtgatctc | ttcagggtgg | ggtggtctct | gataggtagc | 1620 |
| attttccagc | actttgcaag | gaatgttttg | tagctctagg | gtatatatcc | gcctggcatt | 1680 |
| tcacaaaaca | gcctttggga | aatgctgaat | taaagtgaat | tgttgacaaa | tgtaaacatt | 1740 |
| ttcagaaata | ttcatgaagc | ggtcacagat | cacagtgtct | tttggttaca | gcacaaaatg | 1800 |
| atggcagtgt | ttgaaaaac | taaaacagaa | aaaaaatgg | aagccaacac | atcactcatt | 1860 |
| ttaggcaaat | gttaaacat | ttttatctat | cagaatgttt | attgttgctg | gttataagca | 1920 |
| gcaggattgg | ccggctagtg | tttcctctca | tttccctttg | atacagtcaa | caagcctgac | 1980 |
| cctgtaaaat | ggaggtggaa | agacaagctc | aagtgttcac | aacctggaag | tgcttcggga | 2040 |
| agaagggggac | aatggcagaa | caggtgttgg | tgacaattgt | caccaattgg | ataaagcagc | 2100 |
| tcaggttgta | gtgggccatt | aggaaactgt | cggtttgctt | tgatttccct | gggagctgtt | 2160 |
| ctctgtcgtg | agtgtctctt | gtctaaacgt | ccattaagct | gagagtgcta | tgaagacagg | 2220 |

```
atctagaata atcttgctca cagctgtgct ctgagtgcct agcggagttc cagcaaacaa      2280
aatggactca agagagattt gattaatgaa tcgtaatgaa gttggggttt attgtacagt      2340
ttaaaatgtt agatgttttt aattttttaa ataaatggaa tactttttt ttttttttaa      2400 agaaagcaac tttactgaga caatgtagaa agaagttttg ttccgtttct ttaatgtggt      2460
tgaagagcaa tgtgtggctg aagacttttg ttatgaggag ctgcagatta gctaggggac      2520
agctggaatt atgctggctt ctgataatta ttttaaaggg gtctgaaatt tgtgatggaa      2580
tcagatttta acagctctct tcaatgacat agaaagttca tggaactcat gttttttaaag     2640 ggctatgtaa atatatgaac attagaaaaa tagcaacttg tgttacaaaa atacaaacac      2700
atgttaggaa ggtactgtca tgggctaggc atggtggctc acacctgtaa tcccagcatt      2760
ttgggaagct aagatgggtg gatcacttga ggtcaggagt ttgagaccag cctggccaac      2820
atggcgaaac ccctctctac taaaaataca aaaatttgcc aggcgtggtg gcgggtgcct      2880
gtaatcccag ctactgggga ggctgaggca agagaatcgc ttgaaccag gaggcagagg       2940 ttgcagtgag ccgagatcgt gccattgcac tccagcctgg gtgacaaagc gagactccat     3000
ctcaaaaaaa aaaaaaaaaa aaaggaaag aactgtcatg taaacatacc aacatgttta      3060
aacctgacaa tggtgttatt tgaaacttta tattgttctt gtaagcttta actatatctc     3120
tctttaaaat gcaaataat gtcttaagat tcaaagtctg tattttaaaa gcatggcttt      3180
ggctttgcaa aataaaaaat gtgttttgta catgaa                               3216

<210> SEQ ID NO 2
<211> LENGTH: 3479
<212> TYPE: DNA
<213> ORGANISM: Homo sapiens
<220> FEATURE:
<223> OTHER INFORMATION: chemokine (C-C motif) receptor 6 (CCR6, C-C
      CKR-6), transcript variant 2, chemokine receptor-like 3 (CKR-L3),
      G-protein-coupled receptor 29 (GPR29), seven-transmembrane
      receptor, lymphocyte, 22 (STRL22), LARC receptor, CD196, CMKBR6,
      DCR2, DRY6, GPRCY4

<400> SEQUENCE: 2
aactcacacg gcctcttgca aacgttccca aatcttccca gtcggcttgc agagactcct       60
tgctcccagg agataaccag gtaaaggagt atgaaagttt gggtacaaac tcattgctgc      120
aaattgaaaa ccatgcaaag gctgtcttcc tctggggagt tcaatgcctc tcttttttctt    180 atcactttac cattggttgg actttgattc cagggatcct acgattactc aatacgctac     240
aggatataca tggttaacca tttgcatttg ggcaaatagg cgttacttt caataggaag       300 tggcaatcca gaacttgctt tgggcaatt ctagtagctc accgcttttt tcttaatgac       360
tgctagaagc tgcatcttat tgacagatgg tcatcacatt ggtgagctgg agtcatcaga      420
ttgtggggcc cggagtgagg ctgaagggag tggatcagag cactgcctga gagtcacctc     480
tactttcctg ctaccgctgc ctgtgagctg aaggggctga accatacact ccttttttcta   540 caaccagctt gcatttttc tgcccacaat gagcgggaa tcaatgaatt tcagcgatgt       600
tttcgactcc agtgaagatt attttgtgtc agtcaatact tcatattact cagttgattc     660
tgagatgtta ctgtgctcct tgcaggaggt caggcagttc tccaggctat ttgtaccgat     720
tgcctactcc ttgatctgtg tctttggcct cctggggaat attctggtgg tgatcacctt    780
tgctttttat aagaaggcca ggtctatgac agacgtctat ctcttgaaca tggccattgc    840
agacatcctc tttgttctta ctctcccatt ctgggcagtg agtcatgcca ccggtgcgtg    900
ggttttcagc aatgccacgt gcaagttgct aaaaggcatc tatgccatca actttaactg    960
```

```
cgggatgctg ctcctgactt gcattagcat ggaccggtac atcgccattg tacaggcgac    1020
taagtcattc cggctccgat ccagaacact accgcgcagc aaaatcatct gccttgttgt    1080
gtgggggctg tcagtcatca tctccagctc aacttttgtc ttcaaccaaa aatacaacac    1140
ccaaggcagc gatgtctgtg aacccaagta ccagactgtc tcggagccca tcaggtggaa    1200
gctgctgatg ttggggcttg agctactctt tggtttcttt atcccttttga tgttcatgat    1260 attttgttac acgttcattg tcaaaacctt ggtgcaagct cagaattcta aaaggcacaa    1320
agccatccgt gtaatcatag ctgtggtgct tgtgtttctg gcttgtcaga ttcctcataa    1380
catggtcctg cttgtgacgg ctgcaaattt gggtaaaatg aaccgatcct gccagagcga    1440
aaagctaatt ggctatacga aaactgtcac agaagtcctg gctttcctgc actgctgcct    1500
gaaccctgtg ctctacgctt ttattgggca gaagttcaga aactactttc tgaagatctt    1560
gaaggacctg tggtgtgtga aggaagtaa caagtcctca ggcttctcct gtgccgggag    1620
gtactcagaa aacatttctc ggcagaccag tgagaccgca gataacgaca atgcgtcgtc    1680
cttcactatg tgatagaaag ctgagtctcc ctaaggcatg tgtgaaacat actcatagat    1740
gttatgcaaa aaaagtcta tggccaggta tgcatggaaa atgtgggaat taagcaaaat    1800
caagcaagcc tctctcctgc gggacttaac gtgctcatgg gctgtgtgat ctcttcaggg    1860
tggggtggtc tctgataggt agcattttcc agcactttgc aaggaatgtt ttgtagctct    1920
agggtatata tccgcctggc atttcacaaa acagcctttg ggaaatgctg aattaaagtg    1980
aattgttgac aaatgtaaac attttcagaa atattcatga agcggtcaca gatcacagtg    2040
tcttttggtt acagcacaaa atgatggcag tggtttgaaa aactaaaaca gaaaaaaaaa    2100
tggaagccaa cacatcactc attttaggca aatgtttaaa cattttatc tatcagaatg    2160 tttattgttg ctggttataa gcagcaggat tggccggcta gtgtttcctc tcatttccct    2220
ttgatacagt caacaagcct gaccctgtaa aatggaggtg gaaagacaag ctcaagtgtt    2280
cacaacctgg aagtgcttcg ggaagaaggg gacaatggca gaacaggtgt tggtgacaat    2340
tgtcaccaat tggataaagc agctcaggtt gtagtgggcc attaggaaac tgtcggtttg    2400 cttttgatttc cctgggagct gttctctgtc gtgagtgtct cttgtctaaa cgtccattaa    2460
gctgagagtg ctatgaagac aggatctaga ataatcttgc tcacagctgt gctctgagtg    2520
cctagcggag ttccagcaaa caaaatggac tcaagagaga tttgattaat gaatcgtaat    2580
gaagttgggg tttattgtac agtttaaaat gttagatgtt tttaattttt taaataaatg    2640
gaatactttt ttttttttt taaagaaagc aactttactg agacaatgta gaagaagtt    2700 ttgttccgtt tctttaatgt ggttgaagag caatgtgtgg ctgaagactt ttgttatgag    2760
gagctgcaga ttagctaggg gacagctgga attatgctgg cttctgataa ttattttaaa    2820
ggggtctgaa atttgtgatg gaatcagatt ttaacagctc tcttcaatga catagaaagt    2880
tcatggaact catgttttta aagggctatg taaatatatg aacattagaa aaatagcaac    2940
ttgtgttaca aaaatacaaa cacatgttag gaaggtactg tcatgggcta ggcatggtgg    3000
ctcacacctg taatcccagc attttgggaa gctaagatgg gtggatcact tgaggtcagg    3060
agtttgagac cagcctggcc aacatggcga accctctc tactaaaaat acaaaaattt    3120
gccaggcgtg gtggcgggtg cctgtaatcc cagctacttg ggaggctgag gcaagagaat    3180
cgcttgaacc caggaggcag aggttgcagt gagccgagat cgtgccattg cactccagcc    3240
tgggtgacaa agcgagactc catctcaaaa aaaaaaaaaa aaaaaagga aagaactgtc    3300
```

-continued

```
atgtaaacat accaacatgt ttaaacctga caatggtgtt atttgaaact ttatattgtt    3360
cttgtaagct ttaactatat ctctctttaa aatgcaaaat aatgtcttaa gattcaaagt    3420
ctgtattttt aaagcatggc tttggctttg caaaataaaa aatgtgtttt gtacatgaa     3479
```

<210> SEQ ID NO 3
<211> LENGTH: 374
<212> TYPE: PRT
<213> ORGANISM: Homo sapiens
<220> FEATURE:
<223> OTHER INFORMATION: chemokine (C-C motif) receptor 6 (CCR6, C-C
  CKR-6), chemokine receptor-like 3 (CKR-L3), G-protein-coupled
  receptor 29 (GPR29), seven-transmembrane receptor, lymphocyte, 22
  (STRL22), LARC receptor, CD196, CMKBR6, DCR2, DRY6, GPRCY4

<400> SEQUENCE: 3

```
Met Ser Gly Glu Ser Met Asn Phe Ser Asp Val Phe Asp Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
        195                 200                 205

Arg Trp Lys Leu Leu Met Leu Gly Leu Glu Leu Leu Phe Gly Phe Phe
    210                 215                 220

Ile Pro Leu Met Phe Met Ile Phe Cys Tyr Thr Phe Ile Val Lys Thr
225                 230                 235                 240

Leu Val Gln Ala Gln Asn Ser Lys Arg His Lys Ala Ile Arg Val Ile
                245                 250                 255

Ile Ala Val Val Leu Val Phe Leu Ala Cys Gln Ile Pro His Asn Met
            260                 265                 270

Val Leu Leu Val Thr Ala Ala Asn Leu Gly Lys Met Asn Arg Ser Cys
        275                 280                 285

Gln Ser Glu Lys Leu Ile Gly Tyr Thr Lys Thr Val Thr Glu Val Leu
    290                 295                 300

Ala Phe Leu His Cys Cys Leu Asn Pro Val Leu Tyr Ala Phe Ile Gly
305                 310                 315                 320
```

```
Gln Lys Phe Arg Asn Tyr Phe Leu Lys Ile Leu Lys Asp Leu Trp Cys
                325                 330                 335
Val Arg Arg Lys Tyr Lys Ser Ser Gly Phe Ser Cys Ala Gly Arg Tyr
            340                 345                 350
Ser Glu Asn Ile Ser Arg Gln Thr Ser Glu Thr Ala Asp Asn Asp Asn
                355                 360                 365
Ala Ser Ser Phe Thr Met
            370
```

CCR6 COMPOUNDS

CROSS-REFERENCES TO RELATED APPLICATIONS

This application is a continuation of U.S. patent application Ser. No. 15/709,012, filed Sep. 19, 2017, which is a continuation of U.S. patent application Ser. No. 15/074,965, filed Mar. 18, 2016 (now U.S. Pat. No. 9,795,599), which is a continuation of U.S. patent application Ser. No. 14/557,949, filed Dec. 2, 2014 (now U.S. Pat. No. 9,340,509), which claims the benefit of priority to U.S. Patent Application No. 61/910,838, filed Dec. 2, 2013, the disclosures of which are herein incorporated by reference in their entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON AS AN ASCII TEXT FILE

The Sequence Listing written in file-102-1.TXT, created on Jan. 5, 2015, 16,384 bytes, machine format IBM-PC, MS-Windows operating system, is hereby incorporated by reference in its entirety for all purposes.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3:165-183 (1991), Schall, et al., *Curr Opin. Immunol.* 6:865-873 (1994) and Murphy, *Rev. Immun.*, 12:593-633 (1994)). In addition to stimulating chemotaxis, other changes can be selectively induced by chemokines in responsive cells, including changes in cell shape, transient rises in the concentration of intracellular free calcium ions ([Ca2+]), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

There are two main classes of chemokines, CXC (alpha) and CC (beta), depending on whether the first two cysteines are separated by a single amino acid (C—X—C) or are adjacent (C—C). The alpha-chemokines, such as interleukin-8 (IL-8), neutrophil-activating protein-2 (NAP-2) and melanoma growth stimulatory activity protein (MGSA) are chemotactic primarily for neutrophils, whereas beta-chemokines, such as RANTES, MIP-1a, MIP-1b, monocyte chemotactic protein-1 (MCP-1), MCP-2, MCP-3 and eotaxin are chemotactic for macrophages, T-cells, eosinophils and basophils (Deng, et al., *Nature*, 381:661-666 (1996)). The chemokines bind specific cell-surface receptors belonging to the family of G-protein-coupled seven-transmembrane-domain proteins (reviewed in Horuk, *Trends Pharm. Sci.*, 15:159-165 (1994)) which are termed "chemokine receptors."

On binding their cognate ligands, chemokine receptors transduce an intracellular signal though the associated trimeric G protein, resulting in a rapid increase in intracellular calcium concentration. There are at least eleven human chemokine receptors that bind or respond to beta-chemokines and at least seven human chemokine recepotrs that bind to the alpha chemokines. Additionally CX3CR1 (fractalkine receptor) can bind to the fractalkine chemokine, which is distinguished by a series of three amino acids between the first two cysteines. Chemokine receptors, have been implicated as being important mediators of inflammatory and immunoregulatory disorders and diseases, including asthma and allergic diseases, as well as autoimmune pathologies such as rheumatoid arthritis and atherosclerosis.

CCR6 is known to be expressed primarily in B cells, IL17 secreting T cells, regulatory T cells and dendritic cells and shows strong binding to its cognate ligand CCL20 (MIP-3a). It is expressed on approximately 30-60% of adult peripheral blood effector/memory CD4+ T cells. CCR6 is involved in leukocyte homing to inflamed tissue, particularly the skin and lungs and is co-expressed on almost all T cells that have a skin homing phenotype, the CLA+ T cells. Thus CCR6 may be an important player in skin pathologies in which leukocytes participate.

CCR6 expression has been linked to psoriasis in the following manner. In humans, a large majority of skin-homing CD4 T cells in the peripheral blood express CCR6 with a greater degree of CCL20-mediated chemotaxis occurring in T cells isolated from psoriatic patients (Homey, et. al., *JI*, 2000). IL17 secreting cells are central agents in several inflammatory diseases. T cells, such as γδ T cells and TH17 T cells produce IL17 after activation. The pathogenic effects of IL17 have been associated with human diseases such as rheumatoid arthritis (Patel D D et. al., *Ann Rheum Dis* 2013), multiple sclerosis (Zepp J, Wu L, and X Li *Trends Immunol* 2011), and psoriasis (Martin D A et. al., *J Invest Dermatol* 2012). Evidence strongly linking IL17 with psoriasis include gene wide association studies that show strong association between psoriasis and genes upstream (IL-23) or downstream (NFκb) of IL17 signaling pathways as well as efficacy in targeting IL17 in a clinical setting (Martin D A et. al., *J. Invest Dermat.* 2012; Papp et. al., *NEJM*, 2012; Papp et. al., *NEJM*, 2012). In addition to enhanced CCL20-mediated chemotaxis, CCR6+ T cells isolated from psoriatic patients preferentially secrete IL-17A, IL22, and TNFα when compared to healthy controls (Kagami, et. al., *J. Invest. Dermatol.*, 2010). Lastly, ccl20 mRNA was up-regulated in lesional psoriatic skin samples (Homey, et. al., *JI*, 2000; Dieu-Nosjean, et. al., *JEM*, 2000). In mice, CCR6 knock-out mice were protected from IL-23 driven psoriasis. Thus, a multitude of evidence in both mice and men suggest a protective role for CCR6 blockade in psoriasis and psoriasis-like models.

In view of the clinical importance of CCR6, the identification of compounds that modulate CCR6 function represent an attractive avenue into the development of new therapeutic agents. Such compounds and methods for their use are provided herein.

BRIEF SUMMARY OF THE INVENTION

Described herein are compounds having formula (I):

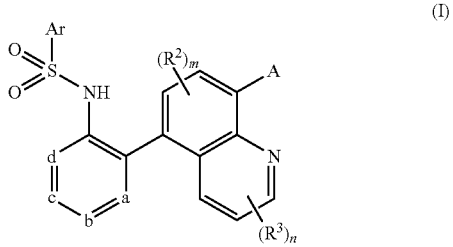

(I)

wherein the ring vertices a, b, c and d; Ar; A; R², R³ and the subscripts m and n have the meanings provided in the Detailed Description below. The compounds have utility in the treatment of diseases or conditions modulated at least in part by CCR6.

Pharmaceutical compositions of the compounds of formula (I) are also provided.

Further provided in the present disclosure preparative methods for the synthesis of compounds of formula (I), as well as selected intermediates useful in the preparation.

BRIEF DESCRIPTION OF THE DRAWINGS

FIGS. 1A-1H provide structures and binding data for compounds prepared and evaluated by the methods described herein. Activity is shown as +, 20000 nM≥IC$_{50}$≥500 nM; ++, 500 nM>IC$_{50}$≥100 nM; +++, 100 nM>IC$_{50}$.

FIGS. 2A-2C provide structures and migration data for compounds prepared and evaluated by the methods described herein. Activity is shown as +, 20000 nM≥IC50≥500 nM; ++, 500 nM>IC50≥100 nM; +++, 100 nM>IC$_{50}$.

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. C$_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., C$_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkane" or "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkane may be a monocyclic, a bicyclic or a polycylic ring system. Non limiting examples of heterocycloalkane groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkane group can be attached to the remainder of the molecule through a ring carbon or a heteroatom.

The term "alkylene" by itself or as part of another substituent means a divalent radical derived from an alkane, as exemplified by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

As used herein, a wavy line, "〜", that intersects a single, double or triple bond in any chemical structure depicted herein, represent the point attachment of the single, double, or triple bond to the remainder of the molecule.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The term "di-(C$_{1-4}$alkyl)amino-C$_{1-4}$ alkyl" refers to an amino group bearing two C$_{1-4}$ alkyl groups that can be the same or different (e.g., methyl, ethyl, propyl, isopropyl, n-butyl, sec-butyl, isobutyl and tert-butyl) and which is attached to the remainder of the molecule through a C$_{1-4}$ alkyl group (a one to four carbon alkylene linking group). Examples of di-(C$_{1-4}$ alkyl)amino-C$_{1-4}$ alkyl groups include dimethylaminomethyl, 2-(ethyl(methyl)amino)ethyl, 3-(dimethylamino)butyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "heteroaryl-alkyl" is meant to include those radicals in which a heteroaryl group is attached to an alkyl group (e.g., pyridylmethyl, thiazolylethyl, and the like).

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^{3}H$), iodine-125 ($^{125}I$) or carbon-14 ($^{14}C$), or non-radioactive isotopes, such as deuterium ($^{2}H$) or carbon-13 ($^{13}C$). Such isotopic variations can provide additional utilities to those described elsewhere with this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The term "and acid isosteres" means, unless otherwise stated, a group which can replace a carboxylic acid, having an acidic functionality and steric and electronic characteristics that provide a level of activity (or other compound characteristic such as solubility) similar to a carboxylic acid. Representative acid isosteres include, hydroxamic acids, sulfonic acids, sulfinic acids, sulfonamides, acyl-sulfonamides, phosphonic acids, phosphinic acids, phosphoric acids, tetrazole, and oxo-oxadiazoles.

Compounds of the invention having formula I can exist in different isomeric forms. As used herein, the terms cis or trans are used in their conventional sense in the chemical arts, i.e., referring to the position of the substituents to one another relative to a reference plane, e.g., a double bond, or a ring system, such as a decalin-type ring system or a hydroquinolone ring system: in the cis isomer, the substituents are on the same side of the reference plane, in the trans isomer the substituents are on opposite sides. Additionally, different conformers are contemplated by the present invention, as well as distinct rotamers. Conformers are conformational isomers that can differ by rotations about one or more a bonds. Rotamers are conformers that differ by rotation about only a single a bond.

II. General

The present invention derives from the discovery that compounds of formula I act as potent antagonists of the CCR6 receptor. The compounds have in vivo anti-inflammatory activity and have superior pharmacokinetic properties. Accordingly, the compounds provided herein are useful in pharmaceutical compositions, methods for the treatment of CCR6-mediated diseases, and as controls in assays for the identification of competitive CCR6 antagonists.

III. Compounds

In one aspect, the present invention provides for a compound of Formula I:

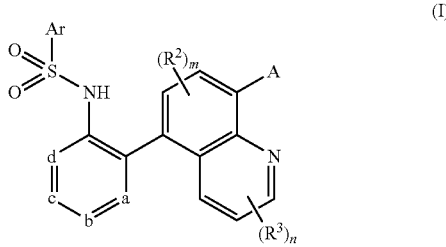

(I)

or a pharmaceutically acceptable salt, hydrate, solvate, N-oxide or rotamer thereof. In Formula (I), the letter A represents a carboxylic acid moiety or a carboxylic acid isostere; ring vertices a, b, c and d are independently selected from the group consisting of N, CH and $C(R^1)$; each $R^1$ is independently selected from the group consisting of halogen, CN, $-SF_5$, $C_{1-8}$ alkyl, $C_{3-8}$ cycloalkyl, $C_{2-8}$ alkenyl, $C_{2-8}$ alkynyl, $C_{1-8}$ haloalkyl, $-OR^a$, $-SR^a$, $-COR^a$, $-NR^aR^b$, and 5- or 6-membered heteroaryl, wherein the alkyl portions of $R^1$ are optionally further substituted with 1-3 $R^a$; and optionally, adjacent $R^1$ members are connected to form an additional 5- or 6-membered ring which is saturated or unsaturated having ring vertices selected from C, O, S and N, wherein the additional 5- or 6-membered ring is optionally substituted with one or two members selected from the group consisting of halogen, hydroxyl, $C_{1-4}$ alkyl, $C_{1-4}$ alkoxy and $C_{1-4}$ haloalkyl; the subscript m is an integer of from 0 to 2; the subscript n is an integer of from 0 to 3; each $R^2$ and $R^3$ is independently selected from the group consisting of halogen, CN, $C_{1-8}$ alkyl, $C_{3-8}$ cycloalkyl, $C_{2-8}$ alkenyl, $C_{2-8}$ alkynyl, $C_{1-8}$ haloalkyl, aryl, $-OR^a$, $-NR^aR^b$ and $-N(R^a)-C_1-C_4$ alkylene-$OR^b$, and wherein the alkyl or aryl portions of $R^2$ and $R^3$ are optionally further substituted with 1-3 $R^a$; Ar is a 5- or 6-membered aromatic or heteroaromatic ring that is optionally substituted with from 1 to 5 $R^4$ substitutents independently selected from the group consisting of halogen, CN, $-SF_5$, $C_{1-8}$ alkyl, $C_{3-8}$ cycloalkyl, $C_{2-8}$ alkenyl, $C_{2-8}$ alkynyl, $C_{1-8}$ haloalkyl, $C_{1-8}$ hydroxyalkyl, $-OR^a$, $-NR^aR^b$, 5- or 6-membered heteroaryl, and 3-, 4-, 5- or 6-membered heterocycloalkane wherein the heteroatoms present as ring vertices of the heteroaryl and heterocycloalkane rings are selected from N, O and S, and wherein the alkyl, cycloalkyl, aryl, heteroaryl and hetereocycloalkane portions of $R^4$ are optionally further substituted with 1-3 $R^a$; each $R^a$ and $R^b$ is independently selected from the group consisting of hydrogen, hydroxyl, halogen, cyano, $C_{1-4}$ alkyl, $C_{1-4}$ alkoxy, $C_{1-4}$ haloalkyl, $C_{3-6}$ cycloalkyl, amino, $C_{1-8}$ alkylamino, and di $C_{1-8}$ alkylamino, or when attached to a nitrogen atom are optionally combined to form a 4- to 7-membered saturated ring, which is optionally substituted with oxo.

In some selected embodiments, the compounds of formula (I) are those wherein ring vertices a, b, c and d are each independently selected from the group consisting of CH and $C(R^1)$. In other selected embodiments, the compounds of formula (I) are those wherein ring vertex d is CH. In still other selected embodiments, the compounds of formula (I) are those wherein ring vertices c and d are each CH. In yet other selected embodiments, the compounds of formula (I) are those wherein ring vertices a, b, and c are each $C(R^1)$. In other selected embodiments, the compounds of formula (I) are those wherein ring vertices a and b are each $C(R^1)$.

In the compounds of formula (I), the letter A represents a carboxylic acid or a carboxylic acid isostere (or a suitable salt thereof). In certain selected embodiments of formula (I), the letter A represents a member selected from the group consisting of $-CO_2H$, $-SO_3H$, $-PO_3H_2$ and a tetrazole. In other selected embodiments, the compounds of formula (I) are those wherein A is a carboxylic acid ($-CO_2H$) or a tetrazole. In some embodiments A is a tetrazole. In some embodiments, A is $-CO_2H$ or a salt thereof.

Turning next to the substituents on the quinoline moiety, in certain selected embodiments m and n are both 0. In other selected embodiments, the compounds of formula (I) are those wherein m and n are independently selected from 0 and 1. For those embodiments wherein $R^2$ and $R^3$ are present, selected embodiments are those wherein each is independently selected from the group consisting of halogen, $C_{1-8}$ alkyl, $-OR^a$, $-NR^aR^b$ and $-N(R^a)-C_1-C_4$ alkylene-$OR^b$, and wherein the alkyl portions of $R^2$ and $R^3$ are optionally further substituted with 1-3 $R^a$.

In other selected embodiments for the compounds of formula (I), and for each of noted embodiments above, Ar is a 6-membered aromatic or heteroaromatic ring selected from the group consisting of benzene, pyridine and pyrimidine, each of which is optionally substituted with from 1-3 $R^4$ substituents. In still other selected embodiments for the compounds of formula (I), and for each of noted embodiments above, Ar is selected from the group consisting of benzene and pyridine, each of which is optionally substituted with from 1-2 $R^4$ substituents.

In one selected group of embodiments of formula (I), Ar is a benzene ring which is optionally substituted with from 1-3 $R^4$ substituents; A is $-CO_2H$; d is CH; and each of a, b and c is independently selected from the group consisting of CH and C(R'). In this group of embodiments, further selected embodiments are those wherein m and n are each independently 0 or 1. Still further selected embodiments are those wherein m and n are each 0.

In other selected embodiments for the compounds of formula (I), and for each of noted embodiments above, the ring having a, b, c and d as ring vertices is selected from the group consisting of:

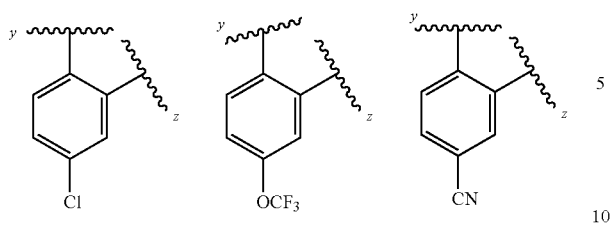

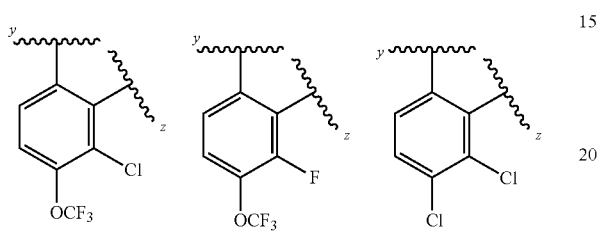

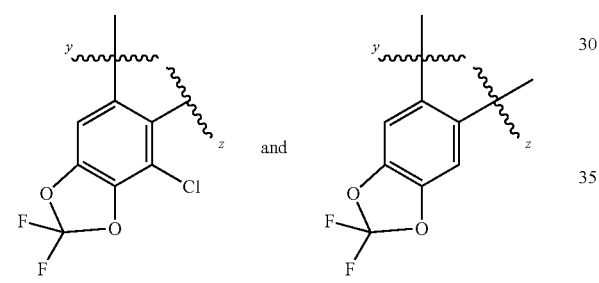

wherein the wavy line labeled y indicates the point of attachment to the NHS(O)₂ portion of the compound and the wavy line labeled z indicates the point of attachment to the quinoline ring.

In other selected embodiments for the compounds of formula (I), and for each of noted embodiments above, Ar is selected from the group consisting of:

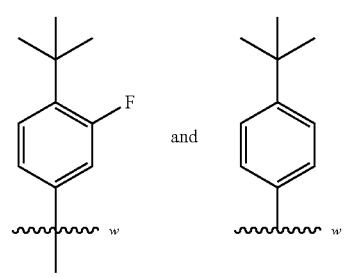 [SMILES: *c1ccc(C(C)(C)C)c(F)c1 ; *c1ccc(C(C)(C)C)cc1]

wherein the wavy line labeled w indicates the point of attachment to the S(O)₂ moiety.

In still other selected embodiments, the compounds of formula (I) are selected from the group consisting of:

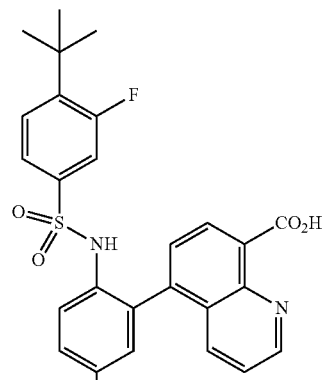

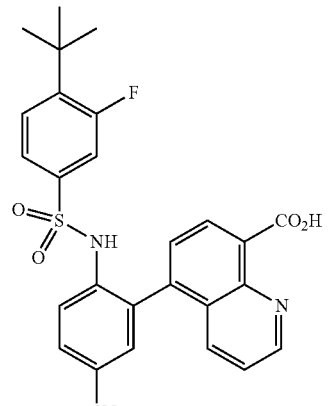

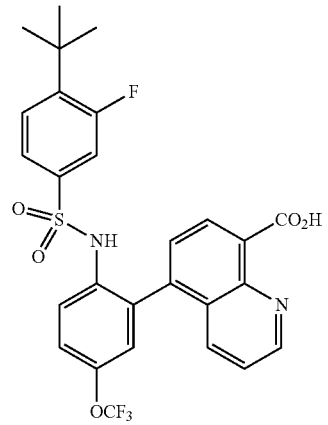

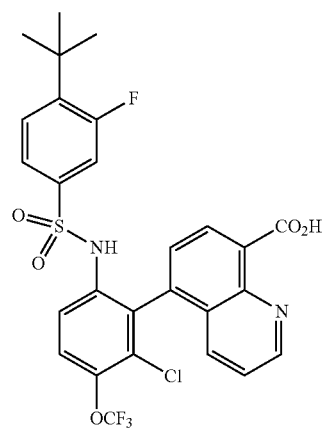

-continued
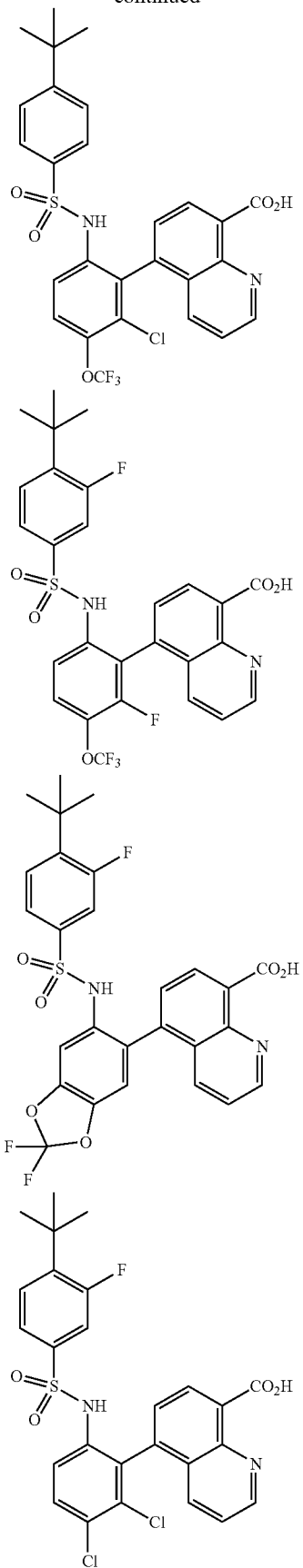
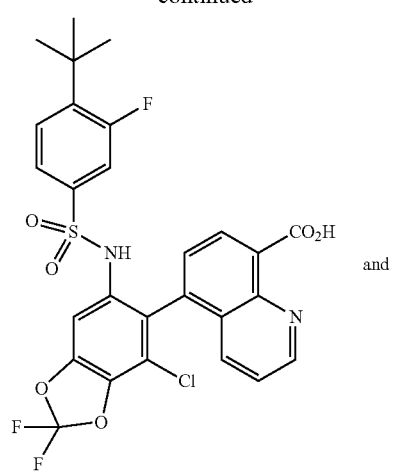
In still other selected embodiments, the compounds of formula (I) are selected from the group consisting of:
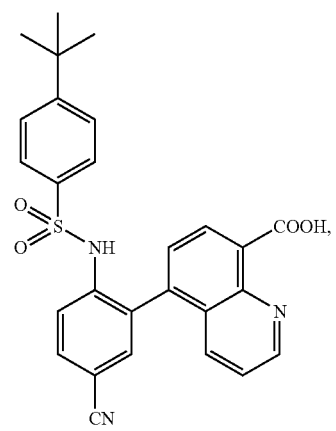

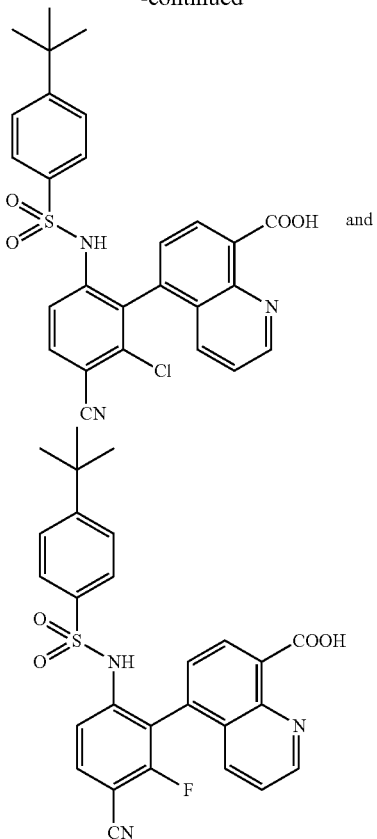

or a pharmaceutically acceptable salt, hydrate, solvate, N-oxide or rotamer thereof.

Preparation of Compounds

The schemes in the Examples below provide certain synthetic routes that can be followed to access certain compounds of the present invention. Other routes or modification of the routes presented below would be readily apparent to a skilled artisan and are within the scope of the present invention.

IV. Pharmaceutical Compositions

In addition the compounds provided above, the compositions for modulating CCR6, activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Pat. No. 6,451,339, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. Pat. No. 5,833,651 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1.

Moreover, as described for example in U.S. Pat. No. 6,770,729, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CCR6

In one aspect, the present invention provides methods of treating or preventing a CCR6-mediated condition or disease by administering to a subject having such a condition or disease, a therapeutically effective amount of any compound of the invention. Preferred compounds for use in the present methods are those compounds provided above as preferred embodiments, as well as compounds specifically exemplified in the Examples below, and provided with specific structures herein. The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the phrase "CCR6-mediated condition or disease" and related phrases and terms refer to a condition or disease characterized by inappropriate, e.g., less than or greater than normal, CCR6 functional activity. Inappropriate CCR6 functional activity might arise as the result of CCR6 expression in cells which normally do not express CCR6, increased CCR6 expression (leading to, e.g., inflammatory and immunoregulatory disorders and diseases) or decreased CCR6 expression. Inappropriate CCR6 functional activity might also arise as the result of CCL20 secretion by cells which normally do not secrete CCL20, increased CCL20 expression (leading to, e.g., inflammatory and immunoregulatory disorders and diseases) or decreased CCL20 expression. A CCR6-mediated condition or disease may be completely or partially mediated by inappropriate CCR6 functional activity. However, a CCR6-mediated condition or disease is one in which modulation of CCR6 results in some effect on the underlying condition or disease (e.g., a CCR6 antagonist results in some improvement in patient well-being in at least some patients).

The term "therapeutically effective amount" means the amount of the subject compound that will elicit the biological or medical response of a tissue, system, animal or human that is being sought by the researcher, veterinarian, medical doctor or other clinician.

Diseases and conditions associated with inflammation, infection and cancer can be treated or prevented with the present compounds and compositions. In one group of embodiments, diseases or conditions, including chronic diseases, of humans or other species can be treated with inhibitors of CCR6 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, Vitiligo (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as arthritis (including rheumatoid and psoriatic) as well as for instance Hashimoto's thyroiditis and Grave's disease, multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout.

Preferably, the present methods are directed to the treatment of diseases or conditions selected from allergic diseases, psoriasis, skin conditions such as atopic dermatitis and asthma and scleroderma.

In another group of embodiments, modulation of CCR6 dependent regulatory T cell trafficking may be modulated to treat diseases or conditions including cancers, infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation.

Those of skill in the art will understand that agents that modulate CCR6 activity can be combined in treatment regimens with other therapeutic agents and/or with chemotherapeutic agents or radiation. In some cases, the amount of chemotherapeutic agent or radiation is an amount which would be sub-therapeutic if provided without combination with a composition of the invention. Those of skill in the art will appreciate that "combinations" can involve combinations in treatments (i.e., two or more drugs can be administered as a mixture, or at least concurrently or at least introduced into a subject at different times but such that both are in the bloodstream of a subject at the same time). Additionally, compositions of the current invention may be administered prior to or subsequent to a second therapeutic regimen, for instance prior to or subsequent to a dose of chemotherapy or irradiation.

The compounds of the present invention are accordingly useful in the prevention and treatment of a wide variety of inflammatory and immunoregulatory disorders and diseases.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prenisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®), Tofacitinib (Xeljanz®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trim eprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, niroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), adalimumab (Humira®), golimumab (Simponi®), rituximab (Rituxan®), tocilizumab (Actemra®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (o) vitamin D3 derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate and leflunomide (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine and proteasome inhibitors such as bortezomib (Velcade®). The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. Examples

The following examples are offered to illustrate, but not to limit the claimed invention.

Reagents and solvents used below can be obtained from commercial sources such as Aldrich Chemical Co. (Milwaukee, Wis., USA). $^1$H-NMR were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In tables, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC equipped with an Agilent Zorbax SB-C18, 2.1×50 mm, 5μ column for sample delivery. Normally the analyte was dissolved in methanol at 0.1 mg/mL and 1 microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:

HPLC, High Pressure Liquid Chromatography; DMF, Dimethyl formamide; TFA, Trifluoroacetic Acid; THF, Tetrahydrofuran; EtOAc, Ethyl acetate; BOC$_2$O, di-tertbutyl dicarbonate or BOC anhydride; HPLC, High Pressure Liquid Chromatography; DIPEA, Diisopropyl ethylamine; HBTU, O-(benzotriazol-1-yl)-N,N,N',N'-tetramethyluronium hexafluorophosphate; dppf, 1,1'-Bis(diphenylphosphino)ferrocene; Pd$_2$(dba)$_3$, Tris(dibenzylideneacetone)dipalladium(0); DIPEA, diisopropylethylamine; DMP, dimethylphthalate; Me, methyl; Et, ethyl; DCM, dichloromethane.

Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1: Synthesis of Methyl 5-(4,4,5,5-tetramethyl-1,3,2-dioxaborolan-2-yl)quinoline-8-carboxylate

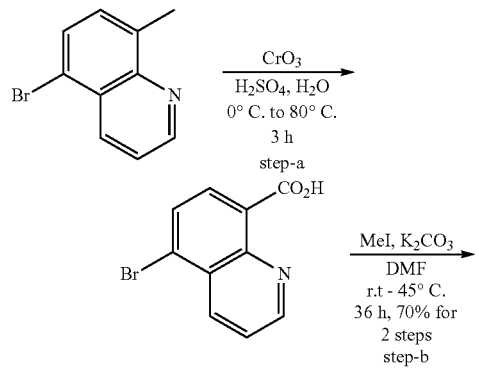

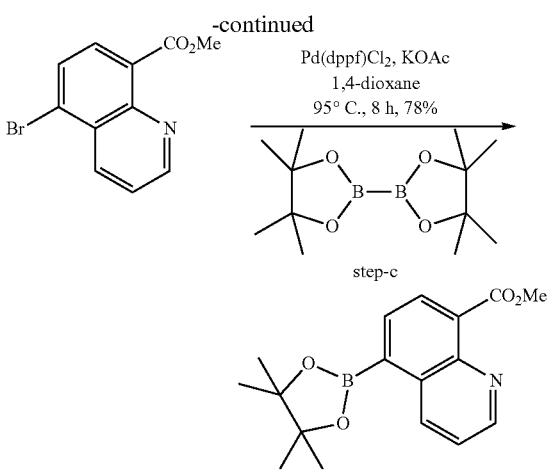

(a) To a stirred solution of H$_2$O (80 mL) and H$_2$SO$_4$ (120 mL) at 0° C. was added 5-bromo-8-methylquinoline (25 g, 112.6 mmol). After obtaining a solution, CrO$_3$ was introduced (16 g, 157.6 mmol) in portion wise while maintaining the internal temperature at 70° C. The reaction mixture was stirred for 1 h at 70° C. An additional CrO$_3$ (16 g, 157.6 mmol) was added in portions and stirred at 80° C. for 2.5 h. After completion of the reaction, it was cooled to r.t, poured onto crushed ice, neutralized with aqueous ammonium hydroxide to get the solids. The solids were filtered, dried under high vacuum for 16 h to get the crude 5-bromoquinoline-8-carboxylic acid (28.0 g) as a green colored solid.

(b) K$_2$CO$_3$ (61.3 g, 444.0 mmol) and methyl iodide (63.1 g, 444.0 mmol) were added to a stirred suspension of 5-bromoquinoline-8-carboxylic acid (28.0 g, 111.0 mmol) in DMF (250 mL) at r.t. The reaction mixture was heated at 45° C. for 36 h, cooled to r.t, filtered the solids, washed with ethyl acetate (100 mL). The filtrate was diluted with water, extracted with ethyl acetate (3×300 mL) and washed with water (3×100 mL). The ethyl acetate layer was dried (Na$_2$SO$_4$), filtered and concentrated under reduced pressure. The residue was purified by flash column chromatography on silica gel, eluting with ethyl acetate in hexanes (0-20%) to afford methyl-5-bromoquinoline-8-carboxylate as a cream color solid (20.5 g, 70% for 2 steps). $^1$H NMR (400 MHz, CDCl$_3$) δ 9.07 (dd, J=4.3, 1.5 Hz, 1H), 8.60 (dd, J=8.7, 1.6 Hz, 1H), 7.88 (s, 2H), 7.58 (dd, J=8.6, 4.0 Hz, 1H), 4.05 (s, 3H)

(c) A solution of methyl-5-bromoquinoline-8-carboxylate (20.5 g, 77.06 mmol), 4,4,5,5-tetramethyl-2-(4,4,5,5-tetramethyl-1,3,2-dioxaborolan-2-yl)-1,3,2-dioxaborolane (21.4 g, 84.7 mmol), and KOAc (18.8 g, 192.6 mmol) in dry 1,4-dioxane (200 mL) was purged with nitrogen gas for 10 min. Then, Pd(dppf)Cl$_2$ (3.14 g, 7.70 mmol) was added and the resulting mixture was heated at 95° C. for 8 h, cooled to r.t and the excess solvent was removed under vacuum. The residue was diluted with ether, filtered through a Celite plug and washed with ether (200 mL); the filtrate was concentrated under reduced pressure. The resulting residue was purified by column chromatography on silica gel, eluting with 0-50% ethyl acetate in hexanes to afford a red color thick syrup/solid which was dissolved in ether and cooled to −20° C. and stored for 12 h, the separated light pink color solid was filtered and dried to get pure methyl 5-(4,4,5,5-tetramethyl-1,3,2-dioxaborolan-2-yl) quinoline-8-carboxylate (17.5 g, 78%): $^1$H NMR (400 MHz, CDCl$_3$) δ 9.14 (dd, J=8.6, 0.6 Hz, 1H), 9.02-9.01 (m, 1H), 8.14 (d, J=7.0 Hz, 1H), 7.94 (d, J=7.0 Hz, 1H), 7.48 (dd, J=8.6, 4.3 Hz, 1H), 4.06 (s, 3H), 1.43 (s, 12H).

Example 2: Synthesis of 3,4-dichloro-2-iodoaniline

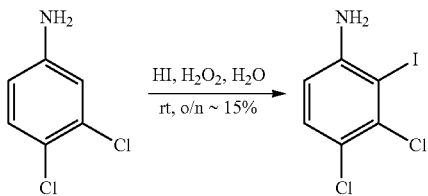 [SMILES: Nc1ccc(Cl)c(Cl)c1 ; Nc1ccc(Cl)c(Cl)c1I]

To a stirred suspension of 3,4-dichloroaniline (20 g, 123 mmol), HI (48%, 15.7 g, 123 mmol), $H_2O_2$ (30%, 8.3 g, 246 mmol) in $H_2O$ (62 mL) at r.t. The reaction mixture was stirred in dark at r.t for overnight. The supernatant was discarded, diluted with ethyl acetate:hexanes (1:10), quenched with saturates $NaHSO_3$, stirred for 1 h at ambient temperature, filtered the solids. The filtrate was washed with water, saturated aqueous $NaHCO_3$, dried (Na2SO4), filtered and concentrated to get 1:4 regioisomeric mixture of iodo derivative (minor isomer is required). It was recrystallized from cyclohexane to afford 1:1 mixture of regioisomers enriched in the filtrate. This mixture was further purified by flash column chromatography on silica gel, eluting with ethyl acetate:hexanes (0-2%) to get the required compound as a cream color solid (5.2 g, ~15% yield). $^1$H NMR (400 MHz, $CDCl_3$) δ 7.22 (d, J=8.6 Hz, 1H), 6.60 (d, J=8.6 Hz, 1H), 4.32 (br, 2H).

Example 3: 3-chloro-2-iodo-4-(trifluoromethoxy)aniline

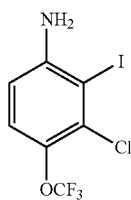

The title compound was synthesized in a similar fashion to Example 2 in 18% yield. $^1$H NMR (400 MHz, $CDCl_3$) δ 7.11 (d, J=8.9 Hz, 1H), 6.67 (d, J=8.9 Hz, 1H), 4.30 (br, 2H).

Example 4: Synthesis of 2-bromo-3-fluoro-4-trifluoromethoxyaniline

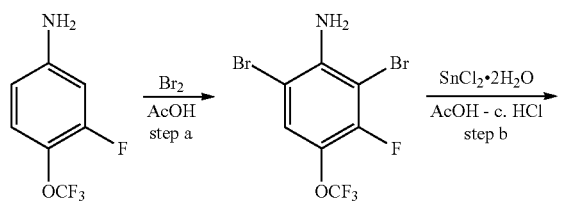

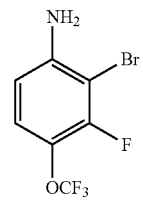

(a) In a 20 mL vial was added 3-fluoro-4-trifluoromethoxyaniline (150 mg, 0.769 mmol) in acetic acid (0.5 mL) at room temperature. Bromine (118 μL, 2.30 mmol, 3 eq.) was added and the reaction was stirred for several hours. Dichloromethane (2 mL) was added to break up the solidified reaction mixture, followed by more bromine (40 μL, 0.781 mmol, 1 eq.) addition. After stirring for another hour, dichloromethane was removed by gently blowing a stream of nitrogen to the reaction mixture. The solid was filtered and washed thoroughly with water and then dried under vacuum to give 2, 6-dibromo-3-fluoro-4-trifluoromethoxyaniline as a white solid (172 mg, 0.489 mmol, 64% yield).

(b) In a 40 mL vial was added 2, 6-dibromo-3-fluoro-4-trifluoromethoxyaniline (172 mg, 0.489 mmol), followed by tin(II) chloride dihydrate (122 mg, 0.540 mmol, 1.1 eq.). Acetic acid (725 μL) and concentrated hydrochloric acid (580 μL) was added to make a solution. The reaction mixture was heated at 115° C. for 1.5 hours. After cooling the reaction to room temperature, most of acetic acid was removed under vacuum. Water was added and the product was extracted with dichloromethane three times. The organic layer was dried over anhydrous sodium sulfate. After removing the solvent under reduced pressure, the crude material was purified using silica gel column chromatography. The recovered 2, 6-dibromo-3-fluoro-4-trifluoromethoxyaniline was eluted using a gradient of 5-10% ethyl acetate in hexanes followed by the desired product, 2-bromo-3-fluoro-4-trifluoromethoxyaniline, which was eluted with 15% ethyl acetate in hexanes (64.8 mg, 0.236 mmol, 48%). $^1$H NMR (400 MHz, $CDCl_3$) δ 7.06 (dd, J=9.0, 9.0 Hz, 1H), 6.52 (dd, J=9.0, 2.0 Hz, 1H), 4.27 (br, 2H).

Example 5: Synthesis of 4-chloro-5-bromo-6-amino-2,2-diflouro-1,3-benzodioxole

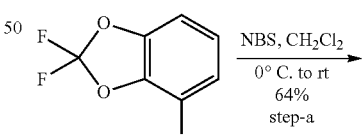

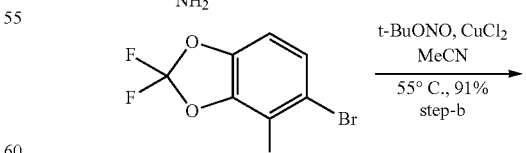

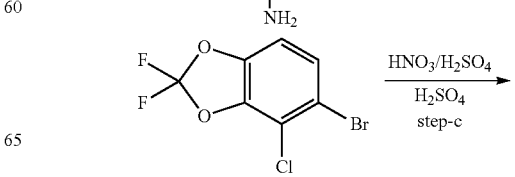

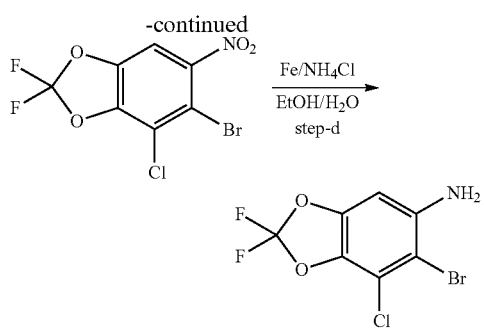

(a) To a stirred solution of 4-amino-2,2-diflouro-1,3-benzodioxole (2.5 g, 14.4 mmol) in dichloromethane at 0° C. was added N-bromosuccinimide (2.7 g, 15.2 mmol) portion wise. The solution was stirred at 0° C. for 30 min, then at room temperature for 1 h. The reaction mixture was quenched with 1M sodium thiosulfate solution and diluted with deionized water, extracted with dichloromethane (2×50 mL). The combined organic layers were dried (Na$_2$SO$_4$), filtered, and concentrated in vacuo. The crude product was purified by flash chromatography (SiO$_2$, 0-20% ethyl acetate in hexanes) to recover starting material 1 g and afford 5-bromo-4-amino-2,2-diflouro-1,3-benzodioxole as colorless oil (2.33 g, 9.25 mmol, 64%). MS: (ES) m/z calculated for C$_7$H$_4$BrF$_2$NO [M+H]$^+$ 252.0, found 252.

(b) To a stirred solution of copper (II) chloride (2.49 g, 18.5 mmol) and tert-butyl nitrite (2.39 g, 23.13 mmol) in acetonitrile at 55° C. was added a solution of 5-bromo-4-amino-2,2-diflouro-1,3-benzodioxole (2.33 g, 9.25 mmol) in acetonitrile. The solution was stirred at 55° C. for 30 min, then cool down to room temperature. The reaction mixture was quenched with 5% hydrochloric acid solution and diluted with deionized water, extracted with ethyl acetate (2×50 mL). The organic layers were dried (Na$_2$SO$_4$), filtered, and concentrated in vacuo. The crude product was purified by flash chromatography (SiO$_2$, 0-20% ethyl acetate in hexanes) to afford 5-bromo-4-chloro-2,2-diflouro-1,3-benzodioxole as yellowish oil (1.5 g, 5.53 mmol, 60%). MS: (ES) m/z calculated for C$_7$H$_2$BrClF$_2$O$_2$ [M+H]$^+$ 272.0, no MS found.

(c) The solution of 5-bromo-4-chloro-2,2-diflouro-1,3-benzodioxole (1.5 g, 5.53 mmol) in 10 mL conc. sulfuric acid was cooled to −10° C. Then a solution of 1 mL fuming nitric acid and 2 mL of conc. sulfuric acid was added drop wise. The resulting solution was stirred at −10° C. for ~2 h. Then the reaction mixture was poured into ice water and a yellow solid precipitated out. Filtered off the solid, rinsed with water and collected the solid. The crude solid was purified by flash chromatography (SiO$_2$, 0-5% ethyl acetate in hexanes) to afford pure 6-nitro-5-bromo-4-chloro-2,2-diflouro-1,3-benzodioxole (1.0 g, 3.16 mmol, 57%). MS: (ES) m/z calculated for C$_7$HBrClF$_2$NO$_4$ [M+H]$^+$ 316.0, found 316.

(d) To the slurry of 6-nitro-5-bromo-4-chloro-2,2-diflouro-1,3-benzodioxole (1.0 g, 3.16 mmol) in ethanol (4 mL) and water (1 mL) was added ammonium chloride (3.38 g, 63.2 mmol) and iron powder (1.06 g, 18.96 mmol). The mixture was warmed up to 90° C. for 1 h and then cooled down. Filtered through a Celite plug and concentrated in vacuo. The crude product was purified by flash chromatography (SiO$_2$, 0-30% ethyl acetate in hexanes) to afford 6-amino-5-bromo-4-chloro-2,2-diflouro-1,3-benzodioxole as a white solid (0.90 g, 3.16 mmol, 100%). MS: (ES) m/z calculated for C$_7$H$_3$BrClF$_2$NO$_2$ [M+H]$^+$ 286.0, found 286.

Example 6: Synthesis of 2,2-difluoro-6-(4,4,5,5-tetramethyl-1,3,2-dioxaborolan-2-yl)benzo-[d][1,3]dioxol-5-amine

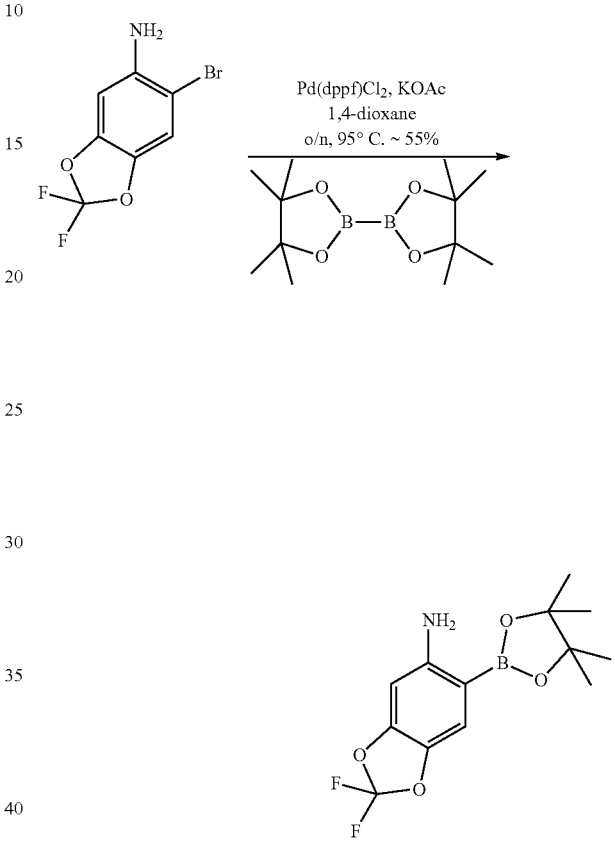

The title compound was synthesized in a similar fashion to Example 1 in 55% yield. $^1$H NMR (400 MHz, CDCl$_3$) δ 7.22 (s, 1H), 6.31 (s, 1H), 4.80 (br, 2H), 1.34 (s, 12H).

Example 7: Synthesis of 2-(4,4,5,5-tetramethyl-1,3,2-dioxaborolan-2-yl)-4-(trifluoromethoxy)aniline

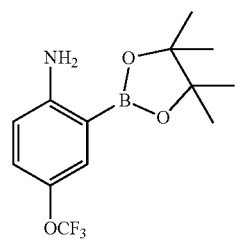 [SMILES: CC1(C)OB(c2cc(OC(F)(F)F)ccc2N)OC1(C)C]

The title compound was synthesized in a similar fashion to Example 1. $^1$H NMR (400 MHz, CDCl$_3$) δ 7.43 (br, 1H), 7.10 (dd, J=4.2, 1.8 Hz, 1H), 6.55 (d, J=7.1 Hz, 1H), 1.34 (s, 12H).

Example 8: Synthesis of 5-[6-[(4-tert-butyl-3-fluorophenyl)sulfonylamino]-2,2-difluoro-1,3-benzodioxol-5-yl]quinoline-8-carboxylic Acid

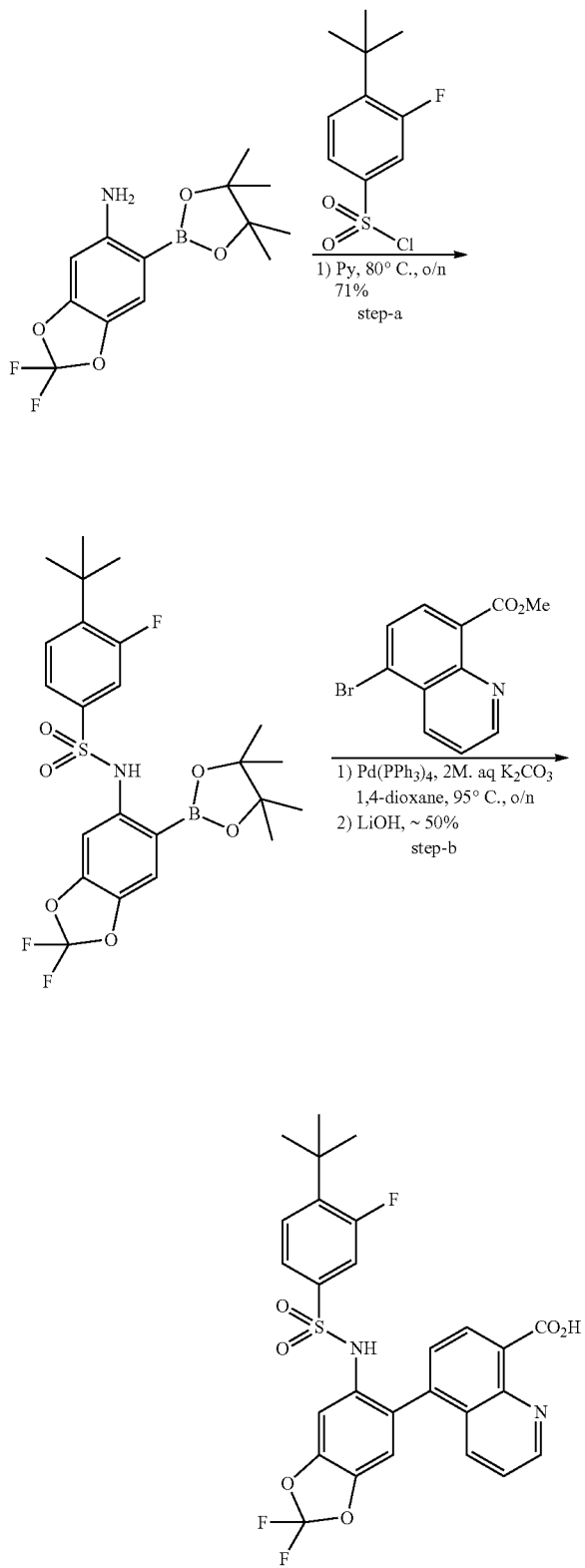

(a) To a solution of 2,2-difluoro-6-(4,4,5,5-tetramethyl-1,3,2-dioxaborolan-2-yl)-1,3-benzodioxol-5-amine (Example 5, 2.7 g, 9.03 mmol) in dry pyridine (12 mL) was added the 4-tert-butyl-3-fluorophenylsulfonyl chloride (2.82 g, 11.28 mmol) and the reaction mixture was heated at 80° C. for overnight. It was cooled to r.t. excess solvent was removed in vacuo. The residue was diluted with saturated aqueous ammonium chloride, extracted with DCM, purified by flash column using hexanes: ethyl acetate mixture as an eluent on silica column to get the pure compound (3.28 g, 71%)

(b) A mixture of the 4-tert-butyl-N-[2,2-difluoro-6-(4,4,5,5-tetramethyl-1,3,2-dioxaborolan-2-yl)-1,3-benzodioxol-5-yl]-3-fluorobenzenesulfonamide (3.2 g, 6.22 mmol), methyl-5-bromoquinoline-8-carboxylate (Example 1, step-b, 1.66 g, 6.22 mmol) and 2 M aq. $K_2CO_3$ (7.8 mL, 15.55 mmol) in 1,4-dioxane (50 mL) was purged with nitrogen for 5 minutes. $Pd(PPh_3)_4$ (360 mg, 0.31 mmol, 5 mol %) was added and the reaction mixture was heated at 95° C. for overnight. The reaction mixture was cooled to r.t. $LiOH.H_2O$ (2.6 g, 62.2 mmol) was added and heated at 80° C. for 1 hour. Cooled to r.t, pH of the reaction medium was adjusted to ~6 with 2N aq.HCl, extracted with ethyl acetate, dried ($Na_2SO_4$), filtered and concentrated. The residue was triturated with methanol to get pure (>95%) title compound as an off-white solid (1.75 g, 50%). $^1$H NMR (400 MHz, $CD_3OD$) δ 8.96-8.94 (m, 1H), 8.57 (d, J=7.4 Hz, 1H), 7.93-7.91 (m, 1H), 7.57-7.54 (m, 2H), 7.42-(t, J=7.8 Hz, 1H), 7.30-7.26 (m, 1H), 7.18-7.15 (m, 1H), 7.05 (d, J=7.5 Hz, 1H), 6.88 (s, 1H), 6.56 (br, 1H), 1.43 (s, 9H); MS: (ES) m/z calculated for $C_{27}H_{21}F_3N_2O_6S$

Example 9: Synthesis of 5-[2-[(4-tert-butyl-3-fluorophenyl)sulfonylamino]-5-(trifluoromethoxy)phenyl]quinoline-8-carboxylic Acid

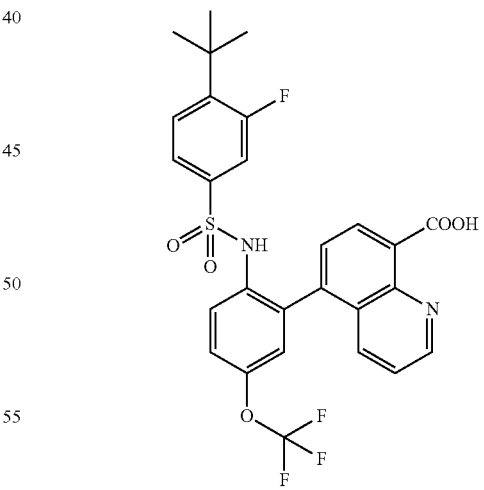

The title compound was synthesized in a similar fashion to Example 8. $^1$H NMR (400 MHz, $CD_3OD$) δ 9.02 (dd, J=4.4, 1.6 Hz, 1H), 8.60 (d, J=7.5 Hz, 1H), 8.07 (dd, J=8.6, 1.7 Hz, 1H), 7.67 (dd, J=8.7, 4.4 Hz, 1H), 7.56 (d, J=8.9 Hz, 1H), 7.47 (ddt, J=9.0, 1.9, 1.1 Hz, 1H), 7.39-7.24 (m, 3H), 7.14 (dd, J=8.3, 2.0 Hz, 1H), 7.03 (dd, J=12.0, 2.0 Hz, 1H), 1.39 (s, 9H); MS: (ES) m/z calculated for $C_{27}H_{22}F_4N_2O_5S$ [M+H]$^+$ 558.12 found 558.1.

Example 10: 5-[2-[(4-tert-butyl-3-fluorophenyl)sulfonylamino]-5-chlorophenyl]quinoline-8-carboxylic Acid

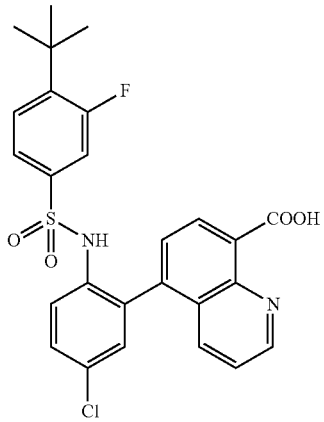 [SMILES: CC(C)(C)c1ccc(S(=O)(=O)Nc2ccc(Cl)cc2-c2ccc(C(=O)O)c3ncccc23)cc1F]

The title compound was synthesized in a similar fashion to Example 8. $^1$H NMR (400 MHz, CD$_3$OD) δ 9.10 (dd, J=4.7, 1.6 Hz, 1H), 8.66 (d, J=7.8 Hz, 1H), 8.27 (dd, J=8.6, 1.6 Hz, 1H), 7.78 (dd, J=8.6, 4.7 Hz, 1H), 7.54 (dd, J=8.6, 2.7 Hz, 1H), 7.41-7.36 (m, 3H), 7.16 (dd, J=8.2, 1.9 Hz, 1H), 7.06 (dd, J=11.1, 1.9 Hz, 1H), 1.40 (s, 9H); MS: (ES) m/z calculated for C$_{26}$H$_{22}$ClFN$_2$O$_4$S [M+H]$^+$ 513.1 found 513.1.

Example 11: Synthesis of 5-[6-[(4-tert-butyl-3-fluorophenyl)sulfonylamino]-2,3-dichlorophenyl]quinoline-8-carboxylic Acid

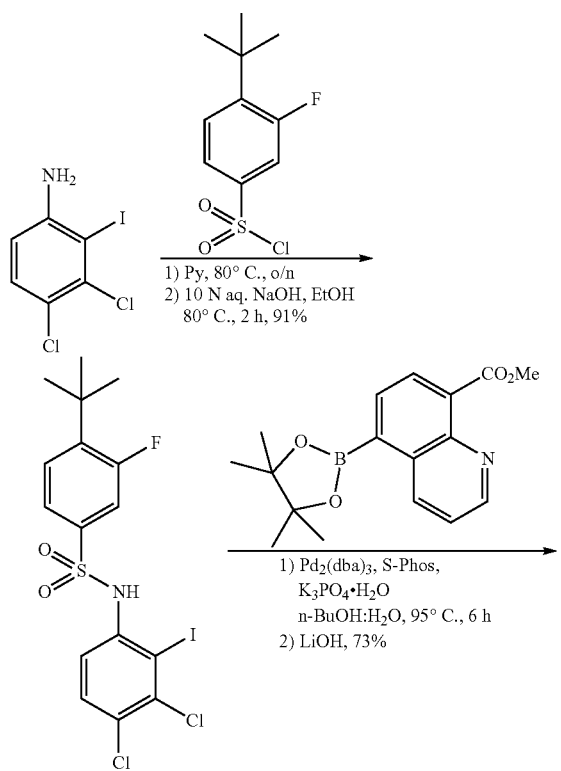

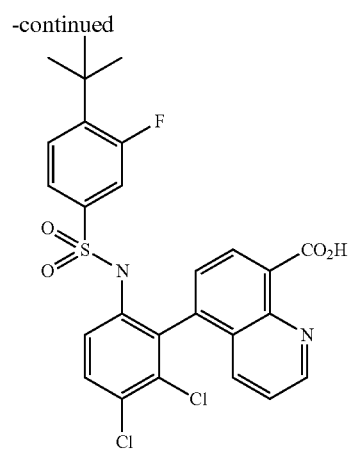

(a) To a solution of 3,4-dichloro-2-iodoaniline (example 2, 2.2 g, 7.67 mmol) in dry pyridine (8 mL) was added 4-tert-butyl-3-fluorophenylsulfonyl chloride (2.11 g, 8.43 mmol) and the reaction mixture was heated at 80° C. for overnight. LCMS indicated presence of mono and bis-sulfonamides. 10 N aq. NaOH (3 mL) and ethanol (2 mL) were added to hydrolyze the bis-sulfonamide. The reaction mixture was then heated at 80° C. for 2 h. It was cooled to r.t, excess solvent was removed in vacuo to afford a dark brown solid, diluted with DCM, washed with 1N aq.HCl, and purified by flash column using hexanes: ethyl acetate mixture as an eluent on silica column to get the pure 4-tert-butyl-N-(3,4-dichloro-2-iodophenyl)-3-fluorobenzsulfonamide as an off white solid (3.5 g, 91%)

(b) A mixture of 4-tert-butyl-N-(3,4-dichloro-2-iodophenyl)-3-fluorobenzsulfonamide (9 g, 17.9 mmol), Methyl 5-(4,4,5,5-tetramethyl-1,3,2-dioxaborolan-2-yl)quinoline-8-carboxylate (7.8 g, 25.1 mmol), K$_3$PO$_4$·H$_2$O (10.3 g, 44.75 mmol) and SPhos (0.73 g, 1.79 mmol) in n-BuOH:H$_2$O (75:25 mL) solvent system was purged with nitrogen for 15 minutes. Then Pd$_2$(dba)$_3$ (0.65 g, 0.72 mmol) was added and heated at 85° C. for 6 h, cooled to r.t, filtered through a Celite plug, washed with ethyl acetate and the filtrate was concentrated in vacuo. The crude product was diluted with THF/H$_2$O (60/10 mL) and lithium hydroxide monohydrate (7.52 g, 179 mmol) was added. The reaction mixture was then heated at 60° C. for overnight, cooled to r.t, the pH was adjusted to ~6 by 2N aq. HCl, extracted with ethyl acetate (3×500 mL), the combined ethyl acetate layer was washed with water, brine, dried (Na$_2$SO$_4$), filtered and concentrated. The residue was purified by flash column using ethyl acetate and hexanes as eluents to get the product which was further triturated from methanol to afford the title compound as an off-white solid (7.2 g, 73%). $^1$H NMR (400 MHz, CDCl$_3$) δ 8.98 (dd, J=4.4, 1.6 Hz, 1H), 8.69 (d, J=7.5 Hz, 1H), 7.77-7.69 (m, 2H), 7.63 (d, J=9.0 Hz, 1H), 7.52 (dd, J=8.6, 4.3 Hz, 1H), 7.42 (t, J=8.0 Hz, 1H), 7.32 (dd, J=4.4, 1.6 Hz, 1H), 7.17 (dd, J=11.4, 2.0 Hz, 1H), 7.05 (d, J=7.5 Hz, 1H), 6.30 (s, 1H), 1.48 (s, 9H); MS: (ES) m/z calculated for C$_{26}$H$_{21}$FN$_2$O$_4$S [M+H]$^+$ 547.06 found 547.1.

Example 12: 5-[2-[(4-tert-butyl-3-fluorophenyl)sulfonylamino]-5-cyanophenyl]quinoline-8-carboxylic Acid Bis Sodium Salt

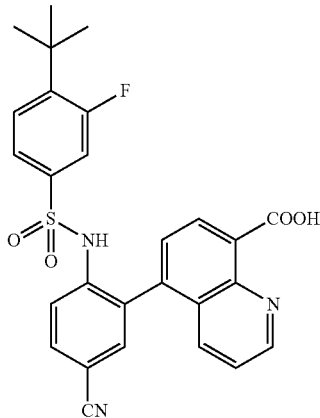 [SMILES: CC(C)(C)c1ccc(S(=O)(=O)Nc2ccc(C#N)cc2-c2ccc(C(=O)O)c3ncccc23)cc1F]

The title compound was synthesized in a similar fashion to Example 11.

0.1 N aq. NaOH (2 eq) was added to the free acid suspended in acetonitrile and water and lyophilized to get the bis sodium salt. $^1$H NMR (400 MHz, CD$_3$OD) δ 9.10 (dd, J=4.8, 1.6 Hz, 1H), 8.69 (d, J=7.5 Hz, 1H), 8.19 (dd, J=8.7, 1.7 Hz, 1H), 7.89 (dd, J=8.5, 2.1 Hz, 1H), 7.81-7.68 (m, 3H), 7.51-7.38 (m, 2H), 7.32 (dd, J=8.3, 2.0 Hz, 1H), 7.22 (dd, J=11.9, 2.0 Hz, 1H), 1.41 (s, 9H); MS: (ES) m/z calculated for C$_{27}$H$_{22}$FN$_3$O$_4$S [M+H]$^+$ 504.13 found 504.

Example 13: Synthesis of 5-[6-[(4-tert-butyl-3-fluorophenyl)sulfonylamino]-2-fluoro-3-(trifluoromethoxy)phenyl]quinoline-8-carboxylic Acid

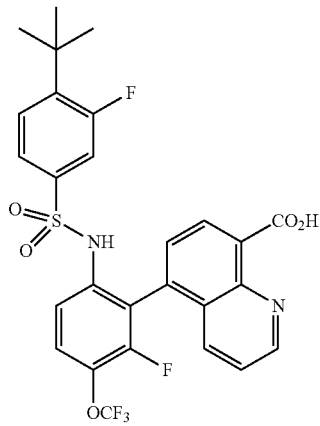 [SMILES: CC(C)(C)c1ccc(S(=O)(=O)Nc2ccc(OC(F)(F)F)c(F)c2-c2ccc(C(=O)O)c3ncccc23)cc1F]

The title compound was synthesized in a similar fashion to Example 11. $^1$H NMR (400 MHz, CDCl$_3$) δ 9.00 (dd, J=4.3, 1.7 Hz, 1H), 8.72 (d, J=7.5 Hz, 1H), 7.86 (dt, J=8.6, 1.5 Hz, 1H), 7.64-7.54 (m, 2H), 7.53-7.33 (m, 3H), 7.30-7.18 (m, 2H), 1.42 (s, 9H); MS: (ES) m/z calculated for C$_{27}$H$_{21}$N$_2$O$_5$SF$_5$ [M−H]$^−$ 579.1, found 579.1.

Example 14: Synthesis of 5-[6-[(4-tert-butylphenyl)sulfonylamino]-2-chloro-3-(trifluoromethoxy)phenyl]quinoline-8-carboxylic Acid Bis Sodium Salt

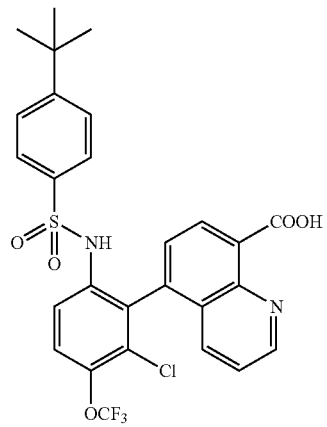 [SMILES: CC(C)(C)c1ccc(S(=O)(=O)Nc2ccc(OC(F)(F)F)c(Cl)c2-c2ccc(C(=O)O)c3ncccc23)cc1]

The title compound was synthesized in a similar fashion to Example 11. $^1$H NMR (400 MHz, CD$_3$OD) δ 8.79-8.77 (m, 1H), 7.72 (d, J=7.4 Hz, 1H), 7.57-7.54 (m, 1H), 7.52 ((d, J=9.4 Hz, 1H), 7.38-7.35 (m, 2H), 7.32-7.29 (m, 2H), 7.23-7.18 (m, 2H), 6.99 (d, J=7.4 Hz, 1H), 1.32 (s, 9H); MS: (ES) m/z calculated for C$_{27}$H$_{22}$ClF$_3$N$_2$O$_5$S [M+H]$^−$ 579.09, found 579.1.

Example 15: Synthesis of 5-[6-[(4-tert-butylphenyl)sulfonylamino]-2-chloro-3-(trifluoromethoxy)phenyl]quinoline-8-carboxylic Acid

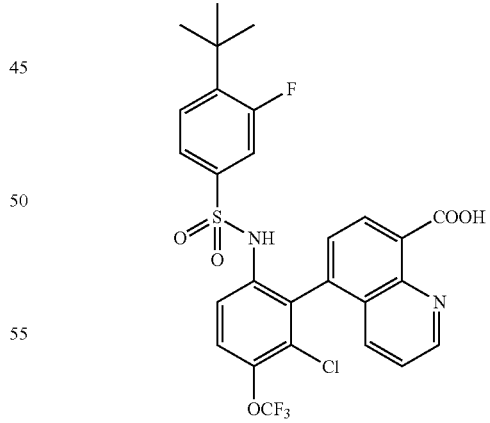

The title compound was synthesized in a similar fashion to Example 11. $^1$H NMR (400 MHz, CD$_3$OD 9.06 (dd, J=4.8, 1.6 Hz, 1H), 8.61 (d, J=8.0 Hz, 1H), 7.94 (dd, J=8.8, 1.6 Hz, 1H), 7.72-7.60 (m, 3H), 7.42 (t, J=8.1 Hz, 1H), 7.20 (dd, J=8.0, 1.6 Hz, 1H), 7.16-7.06 (m, 2H), 1.42 (s, 9H); MS: (ES) m/z calculated for C$_{27}$H$_{21}$ClF$_4$N$_2$O$_5$S [M+H]$^+$ 597.08 found 597.1.

Example 16: Synthesis of 5-[6-[(4-tert-butyl-3-fluorophenyl)sulfonylamino]-4-chloro-2,2-difluoro-1,3-benzodioxol-5-yl]quinoline-8-carboxylic Acid

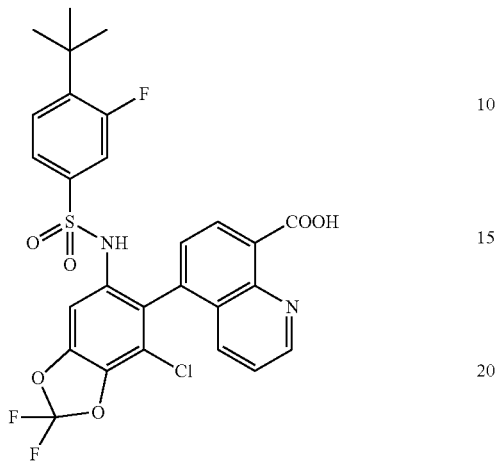

The title compound was synthesized in a similar fashion to Example 11. $^1$H NMR (400 MHz, CD$_3$OD) δ 9.08 (dd, J=4.7, 1.6 Hz, 1H), 8.58 (d, J=7.4 Hz, 1H), 8.11 (dd, J=8.6, 1.6 Hz, 1H), 7.72 (dd, J=8.6, 4.7 Hz, 1H), 7.43-7.39 (m, 2H), 7.18 (dd, J=8.2, 2.0 Hz, 1H), 7.08 (dd, J=10.2, 2.0 Hz, 1H), 1.40 (s, 9H); MS: (ES) m/z calculated for C$_{27}$H$_{20}$ClF$_3$N$_2$O$_6$S [M+H]$^-$ 593.07, found 593.1.

Example 17: Synthesis of 4-tert-butyl-N-[2,2-difluoro-6-[8-(1H-tetrazol-5-yl)-5-quinolyl]-1,3-benzodioxol-5-yl]-3-fluorobenzenesulfonamide

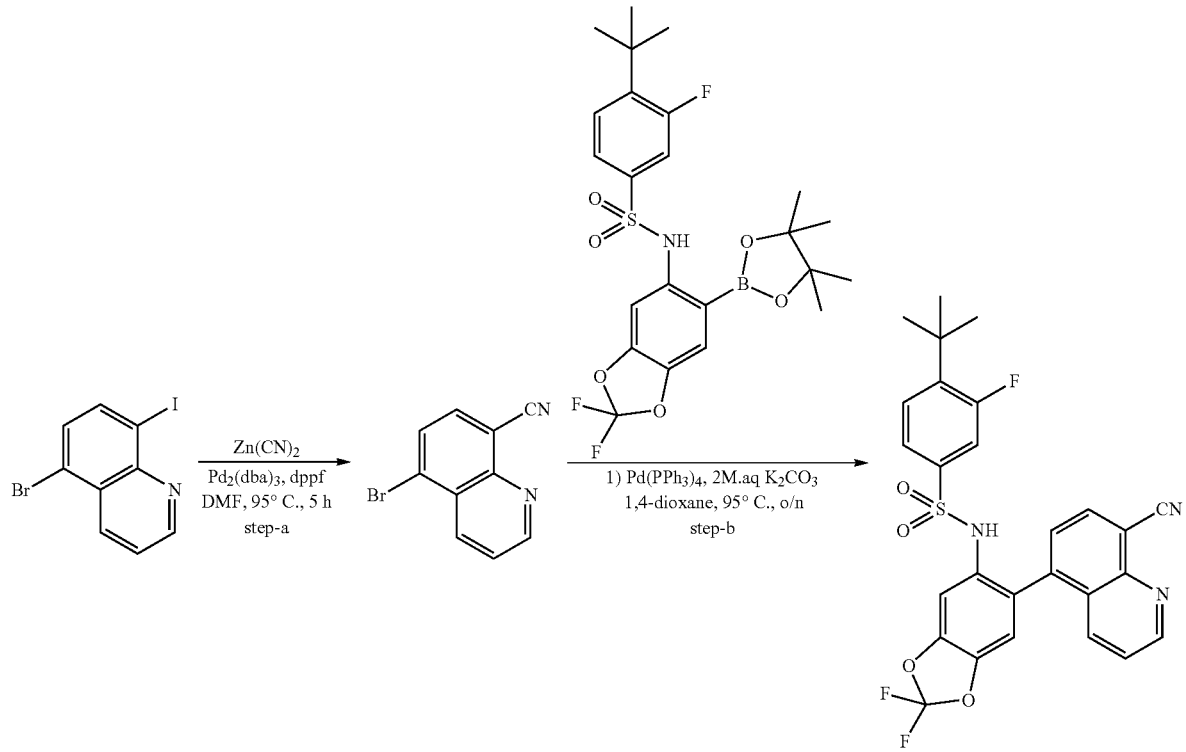

-continued

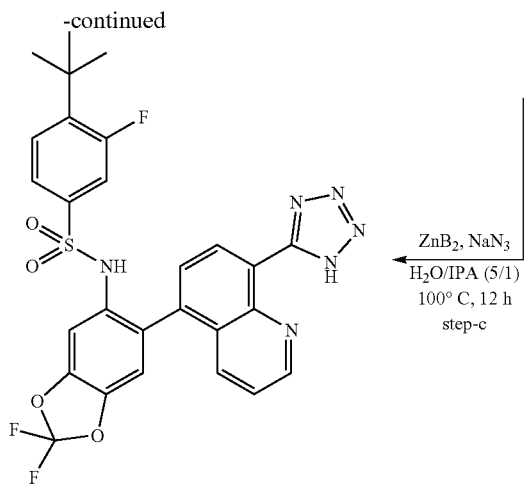

ZnB₂, NaN₃
———————→
H₂O/IPA (5/1)
100° C, 12 h
step-c (a) A mixture of 5-bromo-8-iodoquinoline (0.52 g, 1.55 mmol), Zn(CN)₂ (218 mg, 1.86 mmol), and dppf (103 mg, 0.186 mmol) in DMF (2.5 mL) was purged with N₂ (gas) for 5 minutes. Pd₂(dba)₃ (85 mg, 0.093 mmol) was added and the resulting mixture was heated at 95° C. for 5 h. After completion of the reaction, it was cooled to r.t., diluted with water, and the aqueous solution was extracted with ethyl acetate (3×50 mL). The combined organic layer was washed with brine, dried over Na₂SO₄ and concentrated under reduced pressure. The crude product was purified by column chromatography on silica gel, eluting with ethyl acetate-hexanes (5-25%) to get 5-bromoquinoline-8-carbonitrile as a brown solid (72 mg).

(b) The Suziki reaction was carried out similar to Example 8. 72 mg of the starting material afforded 70 mg of the product.

(c) To a stirred solution of the above nitrile (35 mg, 0.064 mmol) in H₂O/IPA (5:1, 2 mL) at r.t were added ZnBr₂ (43 mg, 0.324 mmol) and NaN₃ (21 mg, 0.324 mmol). The reaction mixture was heated at 100° C. for 16 h. After completion of the reaction, it was cooled to r.t and neutralized with 1N aq. HCl. The aqueous solution was extracted with ethyl acetate (2×25 mL) and the combined organic layers were washed with brine, dried over Na₂SO₄, filtered and concentrated under reduced pressure. The crude product was triturated with methanol to give the title compound as a brownish solid (8 mg). $^1$H NMR (400 MHz, DMSO-d₆) δ 9.84 (s, 1H), 9.04 (dd, J=4.2, 1.7 Hz, 1H), 8.45 (d, J=7.5, Hz, 1H), 7.87 (dd, J=8.6, 1.7 Hz, 1H), 7.58 (dd, J=8.6, 4.2 Hz, 1H), 7.43 (d, J=12.6 Hz, 1H), 7.24 (t, J=8.1, Hz, 1H), 7.16-7.0 (m, 3H), 1.24 (s, 9H); MS: (ES) m/z calculated for $C_{28}H_{22}F_3N_5O_4S$ [M+H]⁺ 582.13 found 582.1.

Example 18: Synthesis of 5-[2-[(4-tert-butylphenyl)sulfonylamino]-5-cyanophenyl]quinoline-8-carboxylic Acid

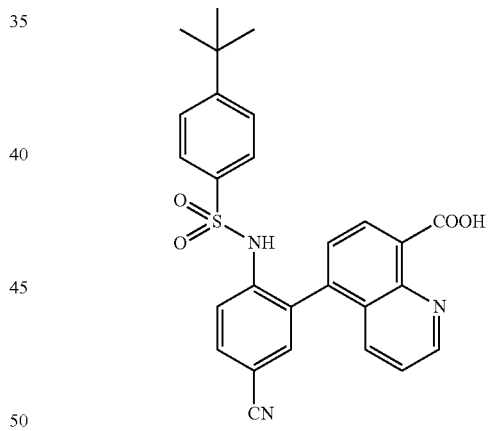

The title compound was synthesized in a similar fashion to Example 11. $^1$H NMR (400 MHz, CDCl₃) δ 9.00 (dd, J=4.3, 1.6 Hz, 1H), 8.68 (d, J=7.4 Hz, 1H), 7.92 (d, J=8.6 Hz, 1H), 7.87 (dd, J=8.6, 1.2 Hz, 1H), 7.78 (dd, J=9.0, 2.0 Hz, 1H), 7.62-7.50 (m, 5H), 7.45 (d, J=7.9 Hz, 1H), 7.19 (d, J=7.5 Hz, 2H), 6.67 (s, 1H), 1.37 (s, 9H); MS: (ES) m/z calculated for $C_{27}H_{23}N_3O_4S$ [M+H]⁺ 486.14 found 486.1.

Example 19: Synthesis of 5-[6-[(4-tert-butylphenyl)sulfonylamino]-2-chloro-3-cyanophenyl]quinoline-8-carboxylic Acid Trifluoroacetic Acid Salt

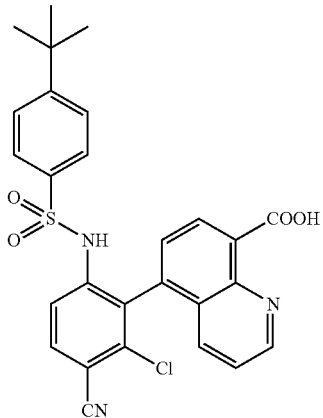

The title compound was synthesized in a similar fashion to Example 11. $^1$H NMR (400 MHz, DMSO-d6) δ 9.85 (bs, 1H), 9.12-9.13 (m, 1H), 8.48 (d, J=7.4 Hz, 1H), δ 8.06 (bs, 1H), 7.89-7.87 (m, 1H), 7.70-7.52 (m, 7H), 7.16 (d, J=6.7 Hz, 1H), 1.30 (s, 9H); MS: (ES) m/z calculated for $C_{27}H_{22}ClN_3O_4S$ [M+H]$^-$ 520.09, found 520.1.

Example 20: Synthesis of 5-[6-[(4-tert-butylphenyl)sulfonylamino]-3-cyano-2-fluorophenyl]quinoline-8-carboxylic Acid Hydrochloric Acid Salt

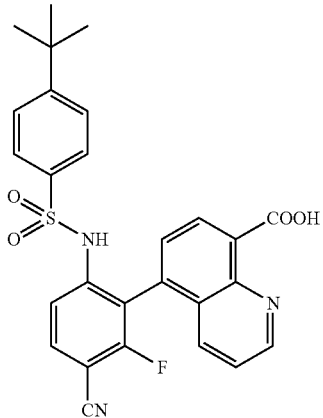

The title compound was synthesized in a similar fashion to Example 11. $^1$H NMR (400 MHz, CDCl$_3$ 9.04 (dd, J=4.3, 1.6 Hz, 1H), 8.76 (d, J=7.4 Hz, 1H), 7.84-7.75 (m, 3H), 7.64-7.53 (m, 5H), 7.22 (d, J=7.4 Hz, 1H), 6.59 (bs, 1H) 1.37 (s, 9H); MS: (ES) m/z calculated for $C_{27}H_{22}FN_3O_4S$ [M+H]$^+$ 504.1 found 504.4.

Biological Example 1: Ligand Binding Assay

Ligand binding assay was used to determine the ability of potential CCR6 antagonists to block the interaction between CCR6 and its ligand CCL20 (MIP3alpha). L1.2 cells stably expressing the CCR6 receptor, were centrifuged and resuspended in assay buffer (20 mM HEPES pH 7.1, 140 mM NaCl, 1 mM CaCl$_2$), 5 mM MgCl$_2$, 0.1% sodium azide and with 0.1% bovine serum albumin) to a concentration of 5×10^5 cells/mL. Binding assays were set up as follows. First, 0.1 mL of cells (5×104 cells/well) was added to the assay plates containing the compounds, giving a final concentration of ~2-10 uM each compound for screening (or part of a dose response for compound IC50 determinations). Then 0.1 mL of $^{125}$I labeled CCL20 (obtained from PerkinElmer; Waltham, Mass.) diluted in assay buffer to a final concentration of ~50 pM, yielding ~30,000 cpm per well, was added, the plates sealed and incubated for approximately 3 hours at 25° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (50 uL; Microscint 20, Packard Instruments) was added to each well, the plates were sealed and radioactivity measured in a Top Count scintillation counter (Packard Instruments). Control wells containing either diluent only (for total counts) or 20 uM compound were used to calculate the percent of total inhibition for compound. The computer program Prism from GraphPad, Inc. (San Diego, Ca) was used to calculate IC50 values. IC50 values are those concentrations required to reduce the binding of labeled TARC to the receptor by 50%. Compounds in FIG. 1 having an IC$_{50}$ value in the binding assay of less than 100 nM are labeled (+++); from 100-500 nM are labeled (++); and less than or equal to 20 μM but above 500 nM are labeled (+).

Biological Example 2: Migration/Chemotaxis Assay

A serum chemotaxis assay was used to determine the efficacy of potential receptor antagonists at blocking the migration mediated through chemokine receptors, such as CCR6. This assay was routinely performed using the ChemoTX® microchamber system with a 5-μm pore-sized polycarbonate membrane. To begin such an assay, chemokine-receptor expressing cells (such as L1.2 cells stably expressing CCR6) were collected by centrifugation at 400×g at room temperature, then suspended at 50 million/ml in human serum. The compound being tested or an equivalent volume of its solvent (DMSO) was then added to the cell/serum mixture at a final DMSO concentration of 0. 25% (v/v). Separately, recombinant human CCL20 was diluted with chemotaxis buffer (HESS+0.1% BSA), generally spanning a range from 0.01 nM to 500 nM, after which 29 μl of diluted chemokine was placed in the lower wells of the ChemoTX® plate. The 5-μm (pore size) polycarbonate membrane was placed onto the plate, and 20 μL of the cell/compound mixture was transferred onto each well of the membrane. The plates were incubated at 37° C. for 90 minutes, after which the polycarbonate membranes were removed and 5 μl of the DNA-intercalating agent CyQUANT (Invitrogen, Carlsbad, Calif.) was added to the lower wells. The amount of fluorescence, corresponding to the number of migrated cells, was measured using a Spectrafluor Plus plate reader (TECAN, San Jose, Calif.).

(a) Evaluation of a Compound of Interest in an Oxazalone Induced Model of DTH

Compounds of the invention were assessed in the murine model of dermal delayed type hypersensitivity (DTH) induced by oxazolone. Briefly, 8-10 week old BALB/c mice were sensitized topically with a 1% solution of oxazolone dissolved in ethanol on their shaved abdomens on day 0. On day 6 post sensitization mice were dosed orally with either vehicle or increasing doses of compounds 1.061 and 1.033 of the invention immediately prior to and 4 hours following a topical challenge with a 0.5% solution of oxazolone in ethanol on the right ear. The following day (day 7), ear thicknesses were measured using caliper measurements. Animals treated with compound had significantly reduced ear swelling compared to vehicle treated controls indicating a compound mediated decrease in oxazolone induced dermal hypersensitivity.

(b) Evaluation of a Compound of Interest in an Imiquimod Induced Model of Psoriasis Multiple mouse models of psoriasis are known. For example, in the Imiquimod-induced mouse model of psoriasis, hair was removed from the back of balb/c mice three days prior to the application of 5% Imiquimod once a day. Vehicle (1% HPMC) or CCR6 compound was administered eg. orally at between 5 and 200 mg/kg once/twice daily at the initiation of Imiquimod application and continued for five to ten days. Therapeutic value was assessed using the following methodologies: daily electronic caliper measurements and immunohistochemistry at the end point to assess skin thickening, flow cytometry and immunofluorescence at the end point to measure leukocyte infiltration and inflammation, and mRNA quantitation via Luminex at days two and five to assess molecular changes. Treatment of animals with compound 1.033 or 1.061 of the invention resulted in a significant improvement in disease.

(c) Evaluation of a Compound of Interest in an IL-23 Induced Model of Psoriasis.

Another method to induce phenotypic changes associated with psoriasis involved intra-dermal injections of IL-23. Briefly, 500 ng of recombinant murine IL-23 was intra-dermally injected every other day into the right ear of C57BL6/N mice for a total of 5-6 administrations over a period of ten to twelve days. Concomitantly, PBS was intra-dermally injected every other day into the left ear of the same mice. CCR6 compound was dosed prophylactically at eg. between 5-200 mg/kg once/twice daily via the oral or other route. Therapeutic dosing was performed by orally providing IL-23 challenged mice with vehicle control for four days. On the fifth day, animals were dosed with a compound of the invention at eg. 5-200 mg/kg once/twice daily via the oral or other route (at this point, two rounds of IL-23 have been intra-dermally injected into the right ear). Efficacy was assessed quantitatively by manually measuring ear thickness using a caliper daily. Treatment of animals with compound 1.033 or 1.061 of the invention resulted in a significant improvement in disease.

(d) Evaluation of a Compound of Interest in a Mouse Model of Septic Shock.

This example describes a procedure to evaluate the efficacy of CCR6 antagonists for treatment of septic shock. An animal model of endotoxic shock can be induced by injecting rodents with lipopolysaccharide (LPS). Three series of mouse groups, comprising 15 mice per group, are treated with an intra-peritoneal injection of an L.D. (lethal dose)-90 of LPS. One series of mice additionally receives phosphate buffered saline (PBS) and Tween 0.5% i.p. 30 minutes before LPS administration. A second series consists of groups of mice receiving different doses of the CCR6 antagonist given either intra-peritoneally, intra-venously, sub-cutaneously, intra-muscularly, orally, or via any other mode of administration 30 minutes before, or concurrently with, LPS administration. A third series of mice, serving as positive control, consists of groups treated with either mouse IL-10 i.p., or anti-TNF antibodies i.p., 30 minutes before LPS administration. Mice are monitored for death for 72 hours following the LPS injection.

(e) Evaluation of a Compound of Interest in a Rodent Model of Asthma/Allergic Lung Inflammation.

CCR6 compounds of the invention can be assessed in a murine model of allergic asthma. Asthma is induced in 8-10 week old BALB/c mice by sensitizing mice with OVA in Alum adjuvant on days 0 and 10. On day 20 mice are challenged with OVA in PBS intranasally to elicit airway inflammation. Groups of mice are either treated with vehicle, or increasing doses of a compound of the invention starting on day 20 and lasting until day 23. Animals are subsequently analyzed at day 23 after the intranasal OVA challenge for cellular infiltrates in bronchoalveolar lavage (BAL). Mice treated with a compound of the invention will display significantly reduced BAL leukocyte numbers relative to vehicle treated mice.

(f) Evaluation of a Compound of Interest in a Mouse Model of Rheumatoid Arthritis.

This example describes a procedure to evaluate the efficacy of CCR6 antagonists for treatment of rheumatoid arthritis. An animal model of rheumatoid arthritis was induced in rodents by injecting them with type II collagen in selected adjuvants. Three series of rodent groups consisting of 15 genetically-susceptible mice or rats per group were injected sub-cutaneously or intra-dermally with type II collagen emulsified in Complete Freund's Adjuvant at days 0 and 21. One series of rodents additionally received PBS and Tween 0.5% i.p. at the initial sensitization and at different dosing schedules thereafter. A second series consists of groups of rodents received different doses of the CCR6 antagonist given either intra-peritoneally, intra-venously, sub-cutaneously, intramuscularly, orally, or via any other mode of administration at the initial sensitization, and at different dosing schedules thereafter. A third series of rodents, serving as positive control, may consist of groups treated with either mouse IL-10 i.p., or anti-TNF antibodies i.p. at the initial sensitization, and at different dosing schedules thereafter. Animals were monitored from weeks 3 till 8 for the development of swollen joints or paws, and graded on a standard disease severity scale. Disease severity was confirmed by histological analysis of joints. Animals treated with compound 1.061 of the invention displayed significantly improved scores following treatment.

(g) Evaluation of a Compound of Interest in a Mouse Model of SLE.

This example describes a procedure to evaluate efficacy of CCR6 antagonists for treatment of Systemic Lupus Erythematosus (SLE). Female NZB/W FI mice spontaneously develop an SLE-like pathology commencing at 6 months of age that is characterized by proteinuria, serum autoantibodies, glomerulonephritis, and eventually death. Three series of NZB/W FI mouse groups comprising 20 mice per group are tested for efficacy of CCR6 antagonist as follows: One series of mice additionally receives phosphate buffered saline (PBS) and Tween 0.5% i.p. soon after weaning, and thereafter at varying dosing schedules. A second series consists of groups of mice receiving different doses of the CCR6 antagonist given either intra-peritoneally, intra-venously, sub-cutaneously, intramuscularly, orally, or via any other mode of administration soon after weaning, and thereafter at varying dosing schedules. A third series of mice, serving as positive control, consists of groups treated with anti-IL10 antibodies given soon after weaning, and thereafter at varying dosing schedules. Disease development is monitored in terms of eventual mortality, kidney histology, serum autoantibody levels, and proteinuria.

(h) Evaluation of a Compound of Interest in a Mouse Model of Malignancy.

This example describes a procedure to evaluate efficacy of CCR6 antagonists for treatment of malignancy. Normal mouse strains can be transplanted with a variety of well-characterized mouse tumor lines, including a mouse thymoma EL4 which has been transfected with OVA to allow easy evaluation of tumor specific antigen responses following vaccination with OVA. Three series of mouse groups from any of these tumor models are tested for CCR6 antagonist efficacy as follows: One series of mice additionally receives PBS and Tween 0.5% i.p. soon after tumor transplant, and thereafter at varying dosing schedules. A second series consists of groups of mice receiving different doses of the CCR6 antagonist given either intra-peritoneally, intra-venously, sub-cutaneously, intramuscularly, orally, or via any other mode of administration soon after tumor transplant, and thereafter at varying dosing schedules. A third series of mice, serving as positive control, consists of groups treated with either anti-IL17 antibodies, anti-IFNg antibodies, given i.p. soon after tumor transplant, and thereafter at varying dosing schedules. Efficacy is monitored via tumor growth versus regression. In the case of the OVA-transfected EL4 thymoma model, cytolytic OVA-specific responses can be measured by stimulating draining lymph node cells with OVA in vitro, and measuring antigen-specific cytotoxicity at 72 hours. Analysis can be performed on eg. tumor mass, IL-17 levels or infiltration of regulatory T cells and treatment with a compound of the invention would be expected to produce a beneficial effect in this model.

(i) Evaluation of a Compound of Interest in a Mouse Carcinoma Model.

The mouse RENCA tumor model accurately mimics the progression of human adult renal cell carcinoma specifically with reference to spontaneous metastasis to lungs and serves as a model for solid tumors. Balb/c 6-8 week old female mice are inoculated with approximately 5e5 RENCA cells (mouse renal adenocarcinoma; ATCC cat # CRL-2947) under the kidney capsule and kidney tumor growth is observed over 22 days, with lung metastasis observed as early as day 15. Animals are dosed with either vehicle or a compound of the invention eg daily subcutaneously, from the time of tumor implantation to monitor effects on primary growth, or at a later time (eg day 7) to monitor the compound effect on metastasis. Primary tumor areas are measured twice a week using mechanical calipers. Tumor volumes are calculated by the formula $v=pab2/6$, where a is the longest diameter and b is the next longest diameter perpendicular to a. A reduction in tumor volume or incidence of metastasis indicates efficacy of compound in this indication.

(j) Evaluation of a Compound of Interest in a Mouse Model of IBD.

This example describes a procedure to evaluate the efficacy of CCR6 antagonists in Inflammatory Bowel Disease (IBD). Several mouse models of IBD (including Crohn's Disease and Ulcerative Colitis) have been developed. Some of these are spontaneous models occurring in genetically engineered transgenic mice that have been depleted of certain cytokine genes (e.g. IL-I0, or IL-2). Another mouse model of IBD is obtained by transferring highly purified populations of CD4+T lymphocytes bearing a particular surface marker phenotype (namely CD45 RB hi) into SCID mice. Three series of mouse groups from anyone of these models can be used to evaluate CCR6 antagonist efficacy as follows. One group of mice additionally receives PBS and Tween 0.5% i.p. soon after weaning in the case of the spontaneous models in transgenic mice, or at time of cell transfer into SCID mice and varying dosings thereafter for the cell transfer model. A second series consists of groups of mice receiving different doses of the CCR6 antagonist given either intraperitoneally, intra-venously, sub-cutaneously, intra-muscularly, orally, or via any other mode of administration soon after weaning in the case of the spontaneous models in transgenic mice, or at time of cell transfer into SCID mice and varying dosings thereafter for the cell transfer model. A third series of mice, serving as positive control, consists of groups treated with antibodies to either IFNg, or TNF, or with cytokine IL-10 soon after weaning in the case of the spontaneous models in transgenic mice, or at time of cell transfer into SCID mice and varying dosings thereafter for the cell transfer model. Mice are evaluated for 6-8 weeks for disease development, monitored initially via weight loss and/or prolapsed rectum, and eventually by histological evaluation of the animals colon and intestinal tract.

```
SEQ ID NO: 1 Human CCR6 mRNA transcript variant 1. ACCESSION NM_004367
VERSION NM_004367.5 GI:150417991
    1    agtgtatggg tgaaggaggc agcagtgtgg ccggagagga gagctgggct gggagcacag 61    gaaggtcccc aggactctgt ggtcatcagt aagagagggc ccacgtgtat atgctggtga 121    acagaaatgt caaccttttc aaagtctgac atttaagaga aaaaactgtg gctgttggtt 181    tgtggaacag acagctcctt ctttattgag tcacctctac tttcctgcta ccgctgcctg 241    tgagctgaag gggctgaacc atacactcct ttttctacaa ccagcttgca tttttctgc 301    ccacaatgag cggggaatca atgaatttca gcgatgtttt cgactccagt gaagattatt 361    ttgtgtcagt caatacttca tattactcag ttgattctga gatgttactg tgctccttgc 421    aggaggtcag gcagttctcc aggctatttg taccgattgc ctactccttg atctgtgtct 481    ttggcctcct ggggaatatt ctggtggtga tcacctttgc tttttataag aaggccaggt 541    ctatgacaga cgtctatctc ttgaacatgg ccattgcaga catcctcttt gttcttactc 601    tcccattctg ggcagtgagt catgccaccg gtgcgtgggt tttcagcaat gccacgtgca 661    agttgctaaa aggcatctat gccatcaact ttaactgcgg gatgctgctc ctgacttgca 721    ttagcatgga ccggtacatc gccattgtac aggcgactaa gtcattccgg ctccgatcca
```

-continued

```
 781   gaacactacc gcgcagcaaa atcatctgcc ttgttgtgtg ggggctgtca gtcatcatct
 841   ccagctcaac ttttgtcttc aaccaaaaat acaacaccca aggcagcgat gtctgtgaac
 901   ccaagtacca gactgtctcg gagcccatca ggtggaagct gctgatgttg gggcttgagc
 961   tactctttgg tttctttatc cctttgatgt tcatgatatt ttgttacacg ttcattgtca
1021   aaaccttggt gcaagctcag aattctaaaa ggcacaaagc catccgtgta atcatagctg
1081   tggtgcttgt gtttctggct tgtcagattc ctcataacat ggtcctgctt gtgacggctg
1141   caaatttggg taaaatgaac cgatcctgcc agagcgaaaa gctaattggc tatacgaaaa
1201   ctgtcacaga agtcctggct ttcctgcact gctgcctgaa ccctgtgctc tacgctttta
1261   ttgggcagaa gttcagaaac tactttctga agatcttgaa ggacctgtgg tgtgtgagaa
1321   ggaagtacaa gtcctcaggc ttctcctgtg ccgggaggta ctcagaaaac atttctcggc
1381   agaccagtga gaccgcagat aacgacaatg cgtcgtcctt cactatgtga tagaaagctg
1441   agtctcccta aggcatgtgt gaaacatact catagatgtt atgcaaaaaa aagtctatgg
1501   ccaggtatgc atggaaaatg tgggaattaa gcaaaatcaa gcaagcctct ctcctgcggg
1561   acttaacgtg ctcatgggct gtgtgatctc ttcagggtgg ggtggtctct gataggtagc
1621   attttccagc actttgcaag gaatgttttg tagctctagg gtatatatcc gcctggcatt
1681   tcacaaaaca gcctttggga aatgctgaat taaagtgaat tgttgacaaa tgtaaacatt
1741   ttcagaaata ttcatgaagc ggtcacagat cacagtgtct tttggttaca gcacaaaatg
1801   atggcagtgg tttgaaaaac taaaacagaa aaaaaaatgg aagccaacac atcactcatt
1861   ttaggcaaat gtttaaacat ttttatctat cagaatgttt attgttgctg gttataagca
1921   gcaggattgg ccggctagtg tttcctctca tttcccttgg atacagtcaa caagcctgac
1981   cctgtaaaat ggaggtggaa agacaagctc aagtgttcac aacctggaag tgcttcggga
2041   agaaggggac aatggcagaa caggtgttgg tgacaattgt caccaattgg ataaagcagc
2101   tcaggttgta gtgggccatt aggaaactgt cggtttgctt tgatttccct gggagctgtt
2161   ctctgtcgtg agtgtctctt gtctaaacgt ccattaagct gagagtgcta tgaagacagg
2221   atctagaata atcttgctca cagctgtgct ctgagtgcct agcggagttc cagcaaacaa
2281   aatggactca agagagattt gattaatgaa tcgtaatgaa gttggggttt attgtacagt
2341   ttaaaatgtt agatgttttt aattttttaa ataaatggaa tactttttt ttttttttaa
2401   agaaagcaac tttactgaga caatgtagaa agaagttttg ttccgtttct ttaatgtggt
2461   tgaagagcaa tgtgtggctg aagactttg ttatgaggag ctgcagatta gctaggggac
2521   agctggaatt atgctggctt ctgataatta ttttaaaggg gtctgaaatt tgtgatggaa
2581   tcagatttta acagctctct tcaatgacat agaaagttca tggaactcat gttttttaaag
2641   ggctatgtaa atatatgaac attagaaaaa tagcaacttg tgttacaaaa atacaaacac
2701   atgttaggaa ggtactgtca tgggctaggc atggtggctc acacctgtaa tcccagcatt
2761   ttgggaagct aagatgggtg gatcacttga ggtcaggagt ttgagaccag cctggccaac
2821   atggcgaaac ccctctctac taaaaataca aaaatttgcc aggcgtggtg gcgggtgcct
2881   gtaatcccag ctacttggga ggctgaggca agagaatcgc ttgaacccag gaggcagagg
2941   ttgcagtgag ccgagatcgt gccattgcac tccagcctgg gtgacaaagc gagactccat
3001   ctcaaaaaaa aaaaaaaaaa aaaggaaag aactgtcatg taaacatacc aacatgttta
3061   aacctgacaa tggtgttatt tgaaacttta tattgttctt gtaagcttta actatatctc
3121   tctttaaaat gcaaataat gtcttaagat tcaaagtctg tatttttaaa gcatggcttt
```

-continued

```
3181    ggctttgcaa aataaaaaat gtgttttgta catgaa
```

SEQ ID N: 2 Human CCR6 mRNA transcript variant 2. ACCESSION NM_031409
VERSION NM_031409.3 GI:150417990

```
   1    aactcacacg gcctcttgca aacgttccca aatcttccca gtcggcttgc agagactcct
  61    tgctcccagg agataaccag gtaaaggagt atgaaagttt gggtacaaac tcattgctgc
 121    aaattgaaaa ccatgcaaag gctgtcttcc tctggggagt tcaatgcctc tcttttttct
 181    atcactttac cattggttgg actttgattc cagggatcct acgattactc aataccctac
 241    aggatataca tggttaacca tttgcatttg ggcaaatagg cgttactttt caataggaag
 301    tggcaatcca gaacttgctt tgggcaatt ctagtagctc accgcttttt cttaatgac
 361    tgctagaagc tgcatcttat tgacagatgg tcatcacatt ggtgagctgg agtcatcaga
 421    ttgtggggcc cggagtgagg ctgaagggag tggatcagag cactgcctga gagtcacctc
 481    tactttcctg ctaccgctgc ctgtgagctg aaggggctga accatacact ccttttccta
 541    caaccagctt gcattttttc tgcccacaat gagcgggaa tcaatgaatt tcagcgatgt
 601    tttcgactcc agtgaagatt atttgtgtc agtcaatact tcatattact cagttgattc
 661    tgagatgtta ctgtgctcct tgcaggaggt caggcagttc tccaggctat ttgtaccgat
 721    tgcctactcc ttgatctgtg tcttttggcct cctggggaat attctggtgg tgatcacctt
 781    tgcttttat aagaaggcca ggtctatgac agacgtctat ctcttgaaca tggccattgc
 841    agacatcctc tttgttctta ctctcccatt ctgggcagtg agtcatgcca ccggtgcgtg
 901    ggttttcagc aatgccacgt gcaagttgct aaaaggcatc tatgccatca actttaactg
 961    cgggatgctg ctcctgactt gcattagcat ggaccggtac atcgccattg tacaggcgac
1021    taagtcattc cggctccgat ccagaacact accgcgcagc aaaatcatct gccttgttgt
1081    gtgggggctg tcagtcatca tctccagctc aacttttgtc ttcaaccaaa aatacaacac
1141    ccaaggcagc gatgtctgtg aacccaagta ccagactgtc tcggagccca tcaggtggaa
1201    gctgctgatg ttggggcttg agctactctt tggttttcttt atcccctttga tgttcatgat
1261    attttgttac acgttcattg tcaaaacctt ggtgcaagct cagaattcta aaaggcacaa
1321    agccatccgt gtaatcatag ctgtggtgct tgtgtttctg gcttgtcaga ttcctcataa
1381    catggtcctg cttgtgacgg ctgcaaattt gggtaaaatg aaccgatcct gccagagcga
1441    aaagctaatt ggctatacga aaactgtcac agaagtcctg gctttcctgc actgctgcct
1501    gaaccctgtg ctctacgctt ttattgggca aagttcaga aactactttc tgaagatctt
1561    gaaggacctg tggtgtgtga aaggaagta caagtcctca ggcttctcct gtgccgggag
1621    gtactcagaa aacatttctc ggcagaccag tgagaccgca gataacgaca atgcgtcgtc
1681    cttcactatg tgatagaaag ctgagtctcc ctaaggcatg tgtgaaacat actcatagat
1741    gttatgcaaa aaaaagtcta tggccaggta tgcatggaaa atgtgggaat taagcaaaat
1801    caagcaagcc tctctcctgc gggacttaac gtgctcatgg gctgtgtgat ctcttcaggg
1861    tggggtggtc tctgataggt agcatttttcc agcactttgc aaggaatgtt ttgtagctct
1921    agggtatata tccgcctggc atttcacaaa acagcctttg ggaaatgctg aattaaagtg
1981    aattgttgac aaatgtaaac attttcagaa atattcatga agcggtcaca gatcacagtg
2041    tcttttggtt acagcacaaa atgatggcag tggtttgaaa aactaaaaca gaaaaaaaaa
2101    tggaagccaa cacatcactc attttaggca aatgtttaaa cattttttatc tatcagaatg
2161    tttattgttg ctggttataa gcagcaggat tggccggcta gtgtttcctc tcatttccct
2221    ttgatacagt caacaagcct gacctgtaa aatggaggtg gaaagacaag ctcaagtgtt
2281    cacaacctgg aagtgcttcg ggaagaaggg gacaatggca gaacaggtgt tggtgacaat
```

```
2341    tgtcaccaat tggataaagc agctcaggtt gtagtgggcc attaggaaac tgtcggtttg 2401    ctttgatttc cctgggagct gttctctgtc gtgagtgtct cttgtctaaa cgtccattaa 2461    gctgagagtg ctatgaagac aggatctaga ataatcttgc tcacagctgt gctctgagtg 2521    cctagcggag ttccagcaaa caaaatggac tcaagagaga tttgattaat gaatcgtaat 2581    gaagttgggg tttattgtac agtttaaaat gttagatgtt tttaattttt taaataaatg 2641    gaatactttt ttttttttt taaagaaagc aactttactg agacaatgta gaaagaagtt 2701    ttgttccgtt tctttaatgt ggttgaagag caatgtgtgg ctgaagactt tgttatgag 2761    gagctgcaga ttagctaggg gacagctgga attatgctgg cttctgataa ttattttaaa 2821    ggggtctgaa atttgtgatg gaatcagatt ttaacagctc tcttcaatga catagaaagt 2881    tcatggaact catgttttta aagggctatg taaatatatg aacattagaa aaatagcaac 2941    ttgtgttaca aaaatacaaa cacatgttag gaaggtactg tcatgggcta ggcatggtgg 3001    ctcacacctg taatcccagc attttgggaa gctaagatgg gtggatcact tgaggtcagg 3061    agtttgagac cagcctggcc aacatggcga aacccctctc tactaaaaat acaaaaattt 3121    gccaggcgtg gtggcgggtg cctgtaatcc cagctacttg ggaggctgag gcaagagaat 3181    cgcttgaacc caggaggcag aggttgcagt gagccgagat cgtgccattg cactccagcc 3241    tgggtgacaa agcgagactc catctcaaaa aaaaaaaaa aaaaaagga agaactgtc 3301    atgtaaacat accaacatgt ttaaacctga caatggtgtt atttgaaact ttatattgtt 3361    cttgtaagct ttaactatat ctctctttaa aatgcaaaat aatgtcttaa gattcaaagt 3421    ctgtattttt aaagcatggc tttggctttg caaataaaa aatgtgtttt gtacatgaa
```

SEQ ID NO: 3 Human CCR6 amino acid sequence
MSGESMNFSDVFDSSEDYFVSVNTSYYSVDSEMLLCSLQEVRQFSRLFVPIAYSLICVFG

LLGNILVVITFAFYKKARSMTDVYLLNMAIADILFVLTLPFWAVSHATGAWVFSNATCK

LLKGIYAINFNCGMLLLTCISMDRYIAIVQATKSFRLRSRTLPRSKIICLVVWGLSVIISSST

FVFNQKYNTQGSDVCEPKYQTVSEPIRWKLLMLGLELLFGFFIPLMFMIFCYTFIVKTLV

QAQNSKRHKAIRVIIAVVLVFLACQIPHNMVLLVTAANLGKMNRSCQSEKLIGYTKTVT

EVLAFLHCCLNPVLYAFIGQKFRNYFLKILKDLWCVRRKYKSSGFSCAGRYSENISRQTS

ETADNDNASSFTM

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

---

What is claimed is:
1. A method of treating psoriasis, comprising administering to a subject in need thereof, a compound selected from the group consisting of,
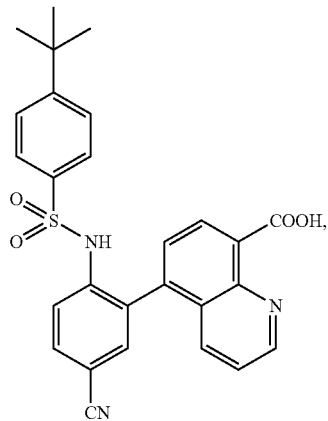
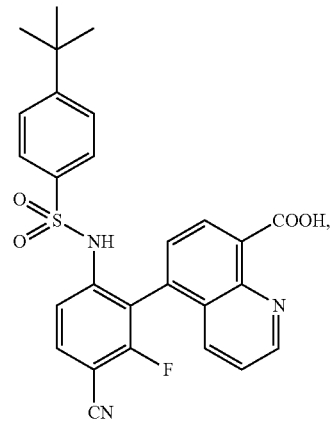
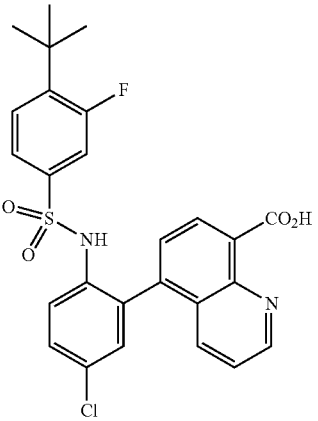
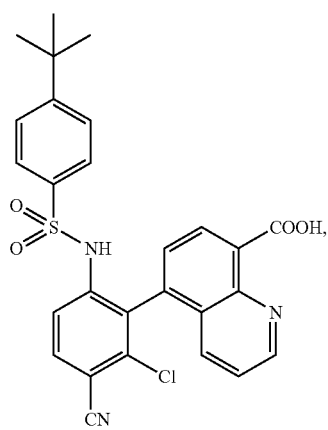
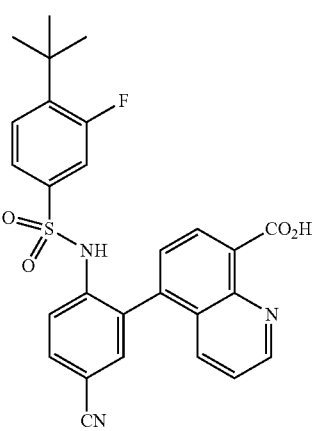

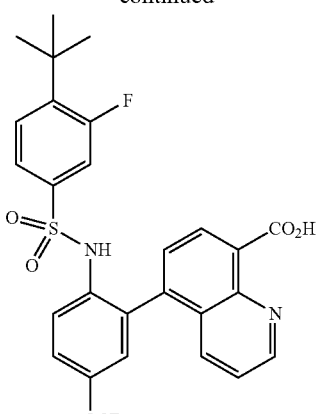
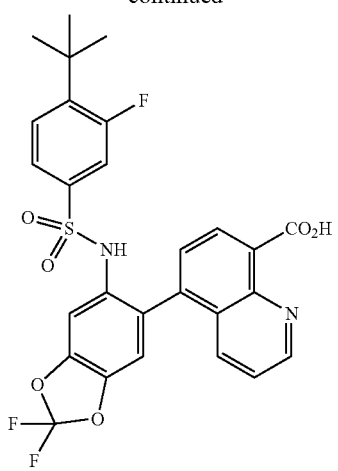

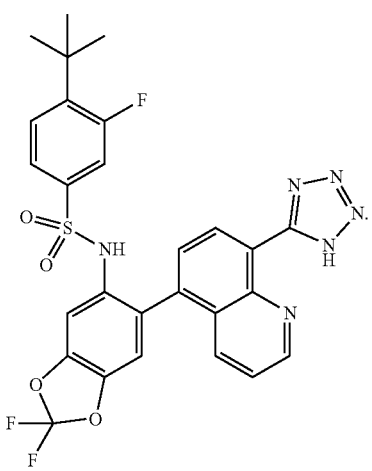

or a pharmaceutically acceptable salt thereof.

2. A method in accordance with claim 1, wherein the compound is selected from the group consisting of:

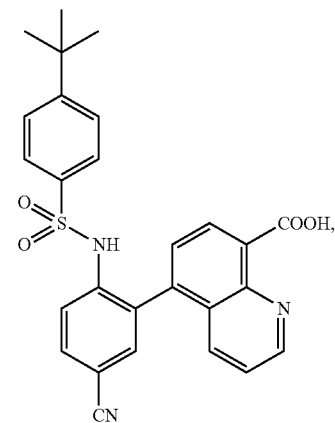

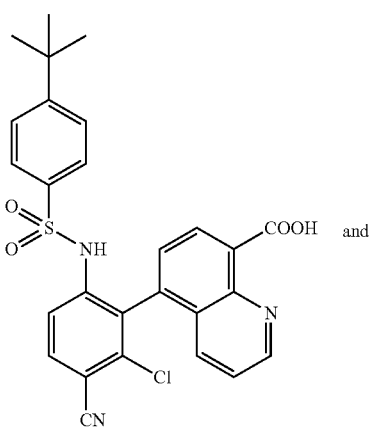

and

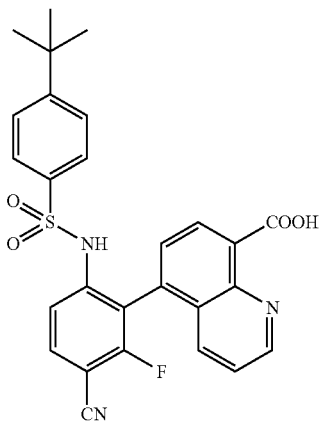 [SMILES: CC(C)(C)c1ccc(S(=O)(=O)Nc2ccc(C#N)c(F)c2-c2ccc(C(=O)O)c3ncccc23)cc1]

or a pharmaceutically acceptable salt thereof.

3. A method in accordance with claim 1, wherein the compound is

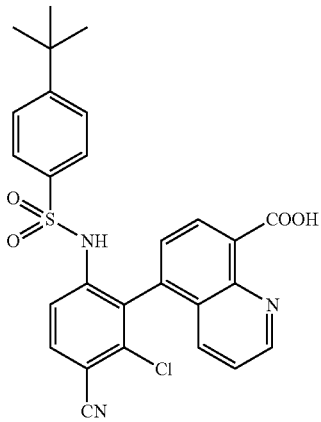 [SMILES: CC(C)(C)c1ccc(S(=O)(=O)Nc2ccc(C#N)c(Cl)c2-c2ccc(C(=O)O)c3ncccc23)cc1]

or a pharmaceutically acceptable salt thereof.

4. A method in accordance with claim 1, wherein the compound is

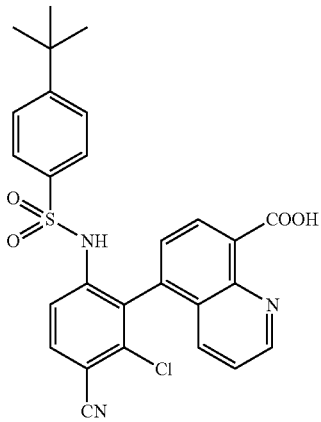 [SMILES: CC(C)(C)c1ccc(S(=O)(=O)Nc2ccc(C#N)c(Cl)c2-c2ccc(C(=O)O)c3ncccc23)cc1]

or a pharmaceutically acceptable salt thereof.

5. A method in accordance with claim 1, wherein the compound is
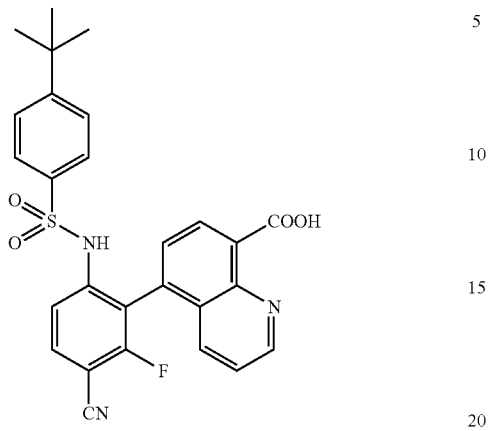
or a pharmaceutically acceptable salt thereof.
* * * * *